United States Patent [19]

Tessier et al.

[11] Patent Number: 4,556,666
[45] Date of Patent: Dec. 3, 1985

[54] CYCLOPROPANE CARBOXYLIC ACID DERIVATIVES

[75] Inventors: Jean Tessier, Vincennes; Jean-Pierre Demoute, Montreuil-sous-Bois; Joseph Cadiergue, Aulnay-sous-Bois, all of France

[73] Assignee: Roussel Uclaf, Paris, France

[21] Appl. No.: 541,084

[22] Filed: Oct. 12, 1983

[30] Foreign Application Priority Data

Oct. 12, 1982 [FR] France ................. 82 17055

[51] Int. Cl.[4] ........................... C07G 121/50
[52] U.S. Cl. ..................... 514/351; 514/389; 514/461; 514/521; 514/531; 260/465 D; 546/300; 548/312; 549/500; 560/124
[58] Field of Search ............... 514/351, 389, 461, 521, 514/531; 260/465 D; 560/124; 546/300; 548/312; 549/500

[56] References Cited

U.S. PATENT DOCUMENTS

| | | | |
|---|---|---|---|
| 3,701,799 | 10/1972 | Fancher ........................... | 260/468 P |
| 3,836,568 | 9/1974 | Hijo et al. ........................ | 260/468 H |
| 4,130,655 | 12/1978 | Drabek et al. ..................... | 560/124 |
| 4,415,748 | 11/1983 | Scharpf et al. .................... | 560/124 |
| 4,423,243 | 12/1983 | Jaotelat et al. .................... | 560/124 |
| 4,431,576 | 2/1984 | Martel et al. ...................... | 560/124 |
| 4,454,343 | 6/1984 | Koudo et al. ...................... | 560/124 |
| 4,464,391 | 8/1984 | Elliot et al. ....................... | 560/124 |
| 4,474,980 | 10/1984 | Bosone et al. ..................... | 560/124 |
| 4,482,570 | 11/1984 | Piccardi et al. .................... | 560/124 |
| 4,489,093 | 12/1984 | Martel et al. ...................... | 560/124 |

FOREIGN PATENT DOCUMENTS 2547534 4/1976 Fed. Rep. of Germany .
2453149 10/1980 France .

Primary Examiner—Joseph L. Schofer
Assistant Examiner—Bernard Lipman
Attorney, Agent, or Firm—Bierman, Peroff & Muserlian

[57] ABSTRACT

All stereoisomeric forms and mixtures of stereoisomers of compounds of the formula

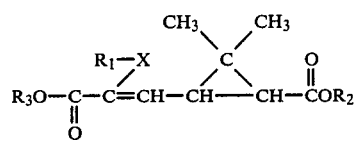

wherein X is selected from the group consisting of oxygen, sulfur, sulfoxide and sulfone, $R_1$ and $R_3$ are individually selected from the group consisting of optionally unsaturated alkyl of 1 to 7 carbon atoms and optionally unsaturated cycloalkyl of 3 to 7 carbon atoms optionally substituted with at least one halogen and optionally interrupted with at least one heteroatom and aryl and aralkyl of 6 to 18 carbon atoms and $R_2$ is the residue of a $R_2OH$ alcohol used in pyrethrinoids synthesis having pesticidal activity and their preparation and novel intermediates.

10 Claims, No Drawings 4,556,666

CYCLOPROPANE CARBOXYLIC ACID DERIVATIVES

STATE OF THE ART

Related pyrethrinoid compounds are described in copending U.S. patent application Ser. No. 495,481 filed May 17, 1983, now U.S. Pat. No. 4,489,093, and in U.S. Pat. Nos. 4,215,069 and 4,291,176.

OBJECTS OF THE INVENTION

It is an object of the invention to provide the novel esters of formula I and novel intermediates and process for their preparation.

It is another object of the invention to provide novel pesticidal compositions and a novel method of combatting pests.

These and other objects and advantages of the invention will become obvious from the following detailed description.

THE INVENTION

The novel compounds of the invention are selected from the group consisting of all stereoisomeric forms and mixtures of stereoisomers of compounds of the formula

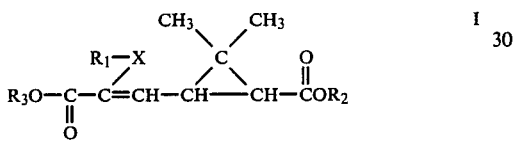

wherein X is selected from the group consisting of oxygen, sulfur, sulfoxide and sulfone, $R_1$ and $R_3$ are individually selected from the group consisting of optionally unsaturated alkyl of 1 to 7 carbon atoms and optionally unsaturated cycloalkyl of 3 to 7 carbon atoms optionally substituted with at least one halogen and optionally interrupted with at least one heteroatom and aryl and aralkyl of 6 to 18 carbon atoms and $R_2$ the residue of a $R_2OH$ alcohol used in pyrethrinoids synthesis.

Among the preferred compounds of formula I are those wherein X is oxygen or sulfur, those wherein $R_2$ is selected from the group consisting of

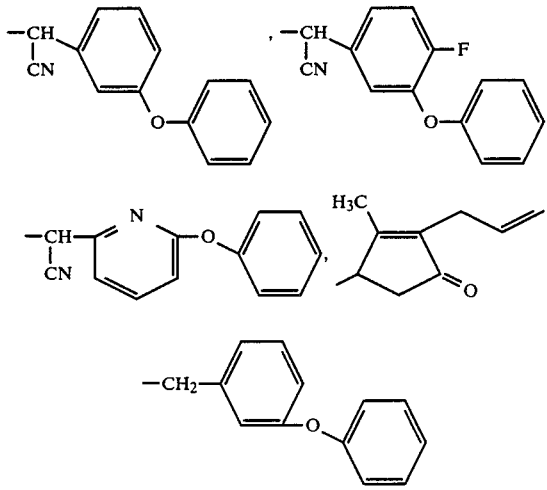

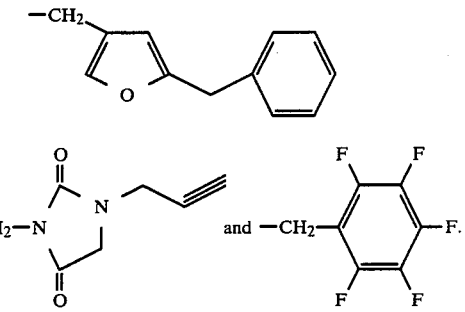

Examples of $R_1$ and $R_3$ are methyl, ethyl, propyl, isopropyl, branched or straight chain butyl, pentyl and hexyl, cyclopropyl, cyclobutyl, cyclopentyl, cyclohexyl, 1-propenyl, 1-butenyl, 1,3-butadienyl, 1-pentenyl, 1-cyclobutenyl, 1-cyclopentenyl, 1-cyclohexenyl,

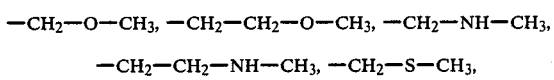

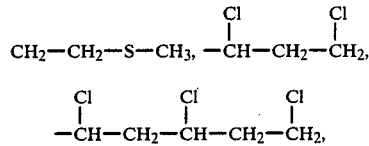

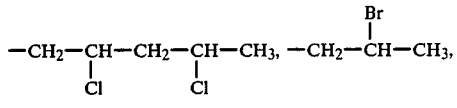

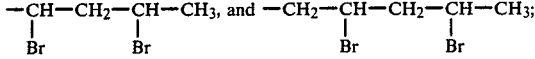

$R_1$ and $R_3$ may also be phenyl, tolyl, xylyl, benzyl,

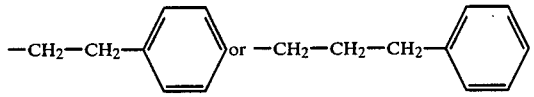

Examples of specific preferred compounds of formula I are (S)α-cyano-3-phenoxy-benzyl (1R,trans,ΔZ) 2,2-dimethyl-3-[2-methoxy-2-methoxycarbonyl-ethenyl]-cyclopropane-carboxylate, (S)α-cyano-3-phenoxy-benzyl (1R,trans,ΔZ) 2,2-dimethyl-3-[2-ethoxy-2-ethoxycarbonyl-ethenyl]-cyclopropane-carboxylate, 3-allyl-2-methyl-4-oxo-2-cyclopenten-1-yl (1R,trans,ΔZ) 2,2-dimethyl-3-[2-methoxy-2-methoxycarbonylethenyl]-cyclopropane-carboxylate, 3-allyl-2-methyl-4-oxo-2-cyclopenten-1-yl (1R,trans,ΔZ) 2,2-dimethyl-3-[2-methoxy-2-methoxycarbonyl-ethenyl]-cyclopropane-carboxylate, [1-(3-propyn-2-yl)-2,5-dioxoimidazolidinyl]-methyl (1R,trans,ΔZ) 2,2-dimethyl-3-[2-methoxy-2-methoxycarbonyl-ethenyl]-cyclopropane-carboxylate, (S)α-cyano-3-phenoxy-4-fluoro-benzyl (1R,trans,ΔZ or ΔE) 2,2-dimethyl-3-[2-methoxy-2-methoxycarbonyl-ethenyl]-cyclopropane-carboxylate, (R,S)α-cyano-6'-phenoxy-2'-pyridyl-methyl (1R,trans,ΔZ or ΔE) 2,2-dimethyl-3-[2-methoxy-2-methoxycarbonyl-ethenyl]-cyclopropane-carboxylate, (S)α-cyano-3-phenoxy-benzyl (1R,trans,ΔZ) 2,2-dimethyl-3-[2-methoxy-2-ethoxycarbonyl-ethenyl]-cyclopropane-carboxylate, (S)α-cyano-3-phenoxy-benzyl (1R,trans,ΔZ) 2,2-dimethyl-3-[2-methoxy-2-methoxycarbonyl-ethenyl]-cyclopropane-carboxylate, (S)α-cyano 3-phenoxy-benzyl (1R,ois∆Z) 2,2-dimethyl-3-[2-methoxy 2-methoxycarbonyl ethenyl]cyclopropane carboxylate, A and B stereoisomers of (S)α-cyano-3-phenoxy-benzyl (1R,cis,ΔZ) 2,2-dimethyl-3-[2-methylsulfinyl-2-methoxycarbonyl-ethenyl]-cyclopropane-carboxylate and (S)α-cyano-3-phenoxy-benzyl (1R,trans,ΔE) 2,2-dimethyl-3-[2-tert.-butoxy-2-methoxycarbonyl-ethenyl]-cyclopropane-carboxylate.

The novel process of the invention for the preparation of formula I comprises reacting a compound of the formula

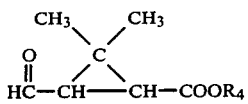

wherein R$_4$ is hydrogen or an easily cleavable ester and in the case R$_4$ is hydrogen, the configuration is cis in the cyclic form of the formula

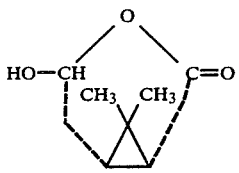

with a compound of the formula

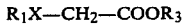         III wherein X, R$_1$ and R$_3$ have the above definition to obtain a compound of the formula

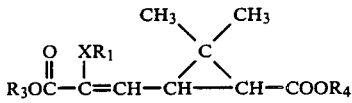         IV and when R$_4$ is an easily cleavable ester, the latter is subjected to a hydrolysis agent to obtain the compound of formula IV wherein R$_4$ is hydrogen and reacting the free acid of formula IV with an alcohol of the formula R$_2$OH or a reactive derivative to obtain the ester of formula I.

In a preferred mode of the process of the invention, the reaction of the compounds of formulae II and III is effected in the presence of a strong base such as an alkali metal alcholate such as potassium tert.-butylate or sodium ethylate. The easily cleavable ester is preferably methoxymethyl, methylthiomethyl or tert.-butyl. The hydrolysis is effected on the easily cleavable ester with an acidolysis agent such as p-toluene sulfonic acid, hydrochloric acid or trifluoroacetic acid and the condensation of the acid of formula IV and the alcohol is preferably effected in the presence of dicyclohexylcarbodiimide or diisopropylcarbodiimide.

In a variation of the process, the compounds of formula IV may be prepared by reacting a compound of formula II with a compound of the formula

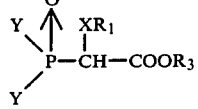         V wherein X, R$_1$ and R$_3$ have the above definition and Y is alkoxy of 1 to 8 carbon atoms or monocyclic aryl of 6 to 8 carbon atoms, preferably in the presence of a strong base such as butyllithium.

In another variation of the process of the invention, the compounds of formula I wherein X is sulfoxide or sulfonyl are prepared by starting with a compound of formulae III or V wherein X is δ and oxidizing the compound of formula I wherein X is sulfur, preferably with an oxidation agent such as sodium metaperiodate or a peracid such as perbenzoic acid or m-chloro-perbenzoic acid.

The compounds of formulae II, III and IV are known in the literature. The compounds of formula IV and especially of the formula

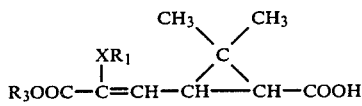         IV' are novel intermediates and are an object of the invention.

Specific preferred compounds of formula IV' are (1R,trans,ΔE) 2,2-dimethyl-3-[2-methoxy-2-methoxycarbonylethenyl]-cyclopropane-carboxylic acid, (1R,trans,ΔZ) 2,2-dimethyl-3-[2-methoxy-2-methoxycarbonyl-ethenyl]-cyclopropanecarboxylic acid, (1R,trans,ΔZ) 2,2-dimethyl-3-[2-methylthio-2-ethoxycarbonyl-ethenyl]-cyclopropane-carboxylic acid, (1R,trans,ΔE or ΔZ) 2,2-dimethyl-3-[2-phenylthio-2-ethoxycarbonylethenyl]-cyclopropane-carboxylic acid, (1R,trans,ΔE) 2,2-dimethyl-3-[2-ethoxy-2-ethoxycarbonyl-ethenyl]-cyclopropanecarboxylic acid, (1R,trans, ΔZ) 2,2-dimethyl-3-[2-ethoxy-2-ethoxylcarbonyl-ethenyl]-cyclopropane-carboxylic acid, (1R,cis,ΔZ) 2,2-dimethyl-3-[2-phenylthio-2-ethoxycarbonyl-ethenyl]-cyclopropane-carboxylic acid, (1R,cis,ΔE or ΔZ) 2,2-dimethyl-3-[2-methoxy-2-methoxycarbonyl-ethenyl]-cyclopropane-carboxylic acid, (1R,cis,ΔE or ΔZ) 2,2-dimethyl-3-[2-methylthio-2-methoxycarbonyl-ethenyl]-cyclopropane-carboxylic acid and (1R,trans,ΔE or ΔZ) 2,2-dimethyl-3-[2-methoxy-2-tert.-butoxycarbonyl-ethenyl]-cyclopropane-carboxylic acid.

The novel pesticidal compositions of the invention are comprised of a pesticidally effective amount of at least one compound of formula I and an inert carrier. The compositions are useful to combat pests such as parasites of vegetables and of warm-blooded animals as well as parasites of premises and are particularly useful to combat insects, nematodes and parasitic acariens which attack warm-blooded animals and vegetables.

The compositions of the invention are particularly useful to combat insects in the agricultural field, for example, to control aphides and larvae of lepidoptera and coleoptera and are usually used at a dose of 10 to 300 g of the compounds of formula I per hectare. The compositions are also useful to combat insects in the premises for example to combat flies, mosquitoes and beetles.

The invention particularly includes insecticidal compositions containing as active principle, at least one compound of formula I. For the compositions intended for premises or agricultural use, the compositions may also contain one or more other pesticidal agents. The compositions may be in the form of powders, granules, suspensions, emulsions, solutions, aerosol solutions, combustible bands, baits and other preparations classically used for compounds of this type.

Besides the active ingredient, the compositions generally contain a vehicle and/or a nonionic surface active agent to ensure a uniform dispersion of the substances in the mixture. The vehicle used may be a liquid such as water, alcohol, hydrocarbons or other organic solvents or a mineral, animal or vegetable oil or a powder such as talc, clays, silicates or Kieselghr or a combustible solid. The insecticidal compositions usually contain 0.005 to 10% by weight of the compounds of formula I.

To increase the biological activity of the compositions of the invention, classical synergists may be incorporated therein such as 1-(2,5,8-trioxadodecyl)-2-propyl-4,5-methylenedioxy-benzene (piperonyl butoxide) or N-(2-ethylheptyl)-bicyclo-[2,2-1] 5-heptene-2,3-dicarboximide or piperonyl-bis-2-(2'-n-butoxy-ethoxy)-ethyl acetal (tropital).

In an advantageous operation for use in premises, the compositions are in the form of fumigants. These compositions advantageously have for their inactive portion a combustible serpentine or coil base or an incombustible fibrous substrate. In the latter case, the fumigant obtained after incorporation of the active ingredient of formula I is placed in a heating apparatus such as an electromosquitoe destroyer. The usual active dose in this case is 0.03 to 95% by weight, preferably.

In the case of a serpentine insecticide, the inert support may be made, for example, of pyrethrum marc, Tabu powder (or Machilus Thumberigii leaf powder), powder of pyrethrum stems, cedar needle powder, sawdust such as pine sawdust, starch and powder of coconut shells. The active dose in this case is preferably 0.03 to 1% by weight.

The compositions of the invention for premises use may be prepared as a spraying oil containing the active ingredient and the oil may soak the wick of a lamp which is then subjected to combustion. The concentration of the compounds of the invention in the oil is preferably 0.03 to 95% by weight.

The compositions have interesting acaricidal properties as demonstrated in classical tests on *Tetranychus urticae*. The test show that the compounds of formula I have a double activity in the control of acariens, namely the classical lethal activity and a repulsive activity which make them particularly interesting from the ecological angle. The compositions are useful as repulsive compositions against vegetable parasites. The compositions may contain other pesticidal agents and/or synergists.

The insecticidal compositions as well as the acaricidal and nematocidal compositions of the invention may also contain one or more other pesticides and are in the usual powder, granule, suspension, emulsion or solution form. For acaricide use, the compositions are preferably wettable powders for foliar spraying containing 1 to 80% of the active ingredient or liquids for foliar spraying containing 1 to 500 g/l of the active ingredient. Also useful are powders for foliar powdering containing 0.05 to 3% by weight of the active ingredient.

For nematocide use, the compositions are in the form of liquids for soil treatment containing 300 to 500 g/l of the active ingredient. For acaricide and nematocide use, the preferred dose of the active compounds is 1 to 100 g per hectare. The compositions have demonstrated nematocidal activity against *Panagrellus silusiae*.

The antifungal compositions of the invention are comprised of an antifungally effective amount of at least one compound of formula I and an inert carrier. Tests have shown the compositions to be useful against *Aerobacter aerogenes, Pseudomonas aeruginoŝa, Botryris cinerea* and *Fusarium roseum*. For fungicidal use, the compositions preferably contain 25 to 95% by weight of the active ingredient for foliar spraying and 2.5 to 99% by weight for foliar powders.

The compositions of the invention may be used to combat animal parasitic acariens such as ticks and sarcoptic parasites such as sarcoptic scabies, psoroptic scabies and chorioptic scabies as well as to combat all sorts of ticks such as Boophilus species, Hyalomnia species, Amblyomnia species and Rhipicephalus species. Tests have shown acaricidal activity against *Rhipicephalus sanguinens* in dogs.

The said medicaments may be administered externally by vaporization, by shampoo, by painting or by bathing. For veterinary usage, the compositions may also be administered by painting the dorsal spine by the "pour on" method as well as being administered digestively or parenterally.

When the compositions are to be used to combat parasitic acariens of animals, the active compounds of the invention are very often incorporated into alimentary compositions in association with a nutritive mixture adapted to the animal to be fed. The nutritive mixture will vary depending upon the specific animal but usually contains cereals, sugars and grains, soybean press cake, peanuts and turnsole, meal of animal origin such as fish meal, synthetic amino acids, mineral salts, vitamins and antioxidants.

Another feature of the invention are insecticidal, acaricidal or nematocidal associations containing as an active ingredient at least one compound of formula I and as a second active ingredient at least one pyrethrinoid ester selected from the group consisting of esters of allethrolones, of 3,4,5,6-tetrahydrophthalimido-methyl alcohol, of 5-benzyl-3-furylmethyl alcohol, of 3-phenoxy-benzyl alcohol and α-cyano-3-phenoxy-benzyl alcohols with chrysanthemic acids, esters of 5-benzyl-3-furyl-methyl alcohol with 2,2-dimethyl-3-(2-oxo-3- tetrahydrothiophenylidene methyl)-cyclopropane-1-carboxylic acids, esters of 3-phenoxy-benzyl alcohol and α-cyano-3-phenoxy-benzyl alcohols with 2,2-dimethyl-3-(2,2-dichlorovinyl)-cyclopropane-1-carboxylic acids, esters of α-cyano-3-phenoxy-benzyl alcohols with 2,2-dimethyl-3-(2,2-dibromovinyl)-cyclopropane-1-carboxylic acids, esters of 3-phenoxybenzyl alcohol with 2-p-chlorophenyl-2-isopropyl-acetic acids, esters of allethrolone, 3,4,5,6-tetrahydrophthalimido-methyl alcohol, 5-benzyl-3-furylmethyl alcohol, 3-phenoxy-benzyl alcohol or α-cyano-3-phenoxy-benzyl alcohols with 2,2-dimethyl-3-(1,2,2,2-tetrahaloethyl)-cyclopropane-1-carboxylic acids where halo is fluorine, chlorine or bromine wherein the compounds of formula I and the above pyrethrinoid esters are in all possible stereoisomer forms.

The latter associated compositions of the invention are of particular interest for combatting by the polyvalence of their action, a large range of parasites or by manifesting a synergistic action in some cases.

The novel method of the invention for combatting parasites such as insects, nematodes, fungus and acariens comprises contacting the parasites with a pesticidally effective amount of at least one compound of formula I.

In the following examples there are described several preferred embodiments to illustrate the invention. However, it should be understood that the invention is not intended to be limited to the specific embodiments.

EXAMPLE 1

(S)α-cyano-3-phenoxy-benzyl (1R,trans,ΔE) 2,2-dimethyl-3-[2-methoxy-2-methoxycarbonyl-ethenyl]-cyclopropane-carboxylate STEP A₁ Tert.-butyl (1R,trans,ΔE and ΔZ) 2,2-dimethyl-3-[2-methoxy-2-methoxycarbonyl-ethenyl]-cyclopropane-carboxylate 21 ml of a solution of 20% butyllithium in cyclohexane was added at −60° C. to a solution of 8.5 g of 1-methoxyacetate-methyl dimethyl phosphonate in 80 ml of tetrahydrofuran and after stirring for 10 minutes at −60° C., a solution of 7.92 g of tert.-butyl (1R,trans) 2,2-dimethyl-3-formylcyclopropane-carboxylate in 25 ml of tetrahydrofuran was added thereto at −60° C. The mixture was stirred at −60° C. for 5 hours and was poured into water. The mixture was stirred and extracted with ether. The decanted organic phase was evaporated to dryness under reduced pressure and the residue was chromatographed over silica gel. Elution with a 9-1 hexane-ethyl acetate mixture yielded 1.23 g of the ΔZ isomer and 6.77 g of the ΔE isomer of tert.-butyl (1R,trans) 2,2-dimethyl-3-[2-methoxy-2-methoxycarbonyl-ethenyl]-cyclopropane-carboxylate.

NMR Spectrum: (deuterochloroform):

ΔZ isomer:

Peaks at 1.22–1.3 ppm (hydrogens of geminal methyls); at 1.47 ppm (hydrogens of methyls of tert.-butyl); at 1.57 to 1.67 ppm and 2.25 to 2.5 ppm (1- and 2-hydrogens of cyclopropyl); at 3.73 and 3.8 ppm (hydrogens of methoxys); at 5.93 to 6.1 ppm (ethylenic hydrogen).

ΔE isomer:

Peaks at 1.13–1.28 ppm (hydrogens of geminal methyls) at 1.45 ppm (hydrogens of methyls of tert.-butyl); at 2.53 to 2.76 ppm (3-hydrogen of cyclopropyl); at 3.6–4.3 ppm (hydrogens of CH₃O—); at 4.9–5.03 ppm (ethylenic hydrogen).

STEP A₂: (1R,trans,ΔE) 2,2-dimethyl-3-[2-methoxy-2-methoxycarbonyl-ethenyl]-cyclopropane-carboxylic acid 9.1 ml of trifuloroacetic acid were added at 0° C. to a solution of 2.13 g of the product of Step A₁ in 40 ml of methylene chloride and the mixture was stirred at 0° C. for 3 hours after which 90 ml of cyclohexane were added. The stirred mixture was evaporated to dryness under reduced pressure and the residue was chromatographed over silica gel. Elution with a 4–6 hexane-ethyl acetate mixture yielded 0.87 g of (1R,trans,ΔE) 2,2-dimethyl-3-[2-methoxy-2-methoxycarbonylethenyl]-cyclopropane-carboxylic acid melting at 78° C.

NMR Spectrum (deuterochloroform):

Peaks at 1.2–1.35 ppm (hydrogens of geminal methyls); at 1.44–1.53 ppm and 2.7–2.9 ppm (1- and 3-hydrogens of cyclopropyl); at 3.60–3.84 ppm(hydrogens of methoxys); at 4.9–5.03 ppm (ethylenic hydrogen).

STEP A₂': (1R,trans, ΔZ) 2,2-dimethyl-3-[2-methoxy-2-methoxycarbonyl-ethenyl]-cyclopropane-carboxylic acid A mixture of 19 g of the product of Step A₁, 1.9 g of p-toluene sulfonic acid and 380 ml of toluene was refluxed for one hour and was evaporated to dryness under reduced pressure. The residue was added to a stirred mixture of water and ether and the decanted organic phase was evaporated to dryness under reduced pressure. The residue was chromatographed over silica gel and was eluted with a 4-6 hexane-ethyl acetate mixture to obtain 7 g of (1R,trans ΔZ) 2,2-dimethyl-3-[2-methoxy-2-methoxycarbonyl-ethenyl]-cyclopropane-carboxylic acid.

NMR Spectrum (deuterochloroform):

Peaks at 1.26–1.37 ppm (hydrogens of geminal methyls); at 1.67–1.75 ppm (1-hydrogen of cyclopropyl); at 2.4–2.47–2.54–2.03 ppm (3-hydrogen of cyclopropyl); at 3.7–3.8 ppm (hydrogens of methoxys); at 5.9–6.06 ppm (ethylenic hydrogen); at 8.3 ppm (hydrogen of —COOH).

STEP B: (S)α-cyano-3-phenoxy-benzyl (1R,trans,ΔE) 2,2-dimethyl-3-[2-methoxy-2-methoxycarbonyl-ethenyl]-cyclopropanecarboxylate A mixture of 1.45 g of 1-chloro-N,N,2-trimethyl-propenylamine, 1.7 g of (1R,trans,ΔE) 2,2-dimethyl-3-[2-methoxy-2-methoxycarbonyl-ethenyl]-cyclopropane-carboxylic acid and 14 ml of methylene chloride was stirred for 30 minutes and a solution of 1.7 g of (S)α-cyano-3-phenoxy-benzyl alcohol, 1.47 g of pyridine and 14 ml of methylene chloride was added thereto. The mixture was stirred for 3 hours at 20° C. and was poured with stirring into 1N hydrochloric acid solution. The decanted organic phase was washed with water and evaporated to dryness under reduced pressure. The residue was chromatographed over silica gel and was eluted with an 8-2 hexane-ethyl acetate mixture to obtain 2.7 g of (S)α-cyano-3-phenoxy-benzyl (1R,trans,ΔE) 2,2-dimethyl-3-[2-methoxy-2-methoxycarbonyl-ethenyl]-cyclopropane-carboxylate.

NMR Spectrum (deuterochloroform):

Peaks at 1.16–1.28 ppm (hydrogens of geminal methyls); at 1.5–1.6 ppm (1-hydrogen of cyclopropyl); at 2.74–2.83–2.88–2.97 ppm (3-hydrogen of cyclopropyl); at 3.6–3.85 ppm (hydrogens of methoxys); at 4.9–5.0 ppm (ethylenic hydrogen); at 6.45 ppm (hydrogen on carbon attached to —CN).

EXAMPLE 2

3-phenoxy-benzyl (1R,trans,ΔE) 2,2-dimethyl-3-[2-methoxy-2-methoxycarbonyl-ethenyl]-cyclopropane-carboxylate A mixture of 2.28 g of (1R,trans,ΔE) 2,2-dimethyl-3-[2-methoxy-2-methoxycarbonyl-ethenyl]-cyclopropane-carboxylic acid, 20 ml of methylene chloride, 2.06 g of dicyclohexylcarbodiimide and 1 ml of pyridine was stirred at 20° C. for 45 minutes and after the addition of a solution of 2 g of 3-phenoxy-benzyl alcohol in 5 ml of methylene chloride, the mixture was stirred at 20° C. for 16 hours and was filtered. The filtrate was evaporated to dryness under reduced pressure and the residue was chromatographed over silica gel. Elution with a 7-3 hexane-ethyl acetate mixture yielded 1.6 g of 3-phenoxy-benzyl (1R,trans,ΔE) 2,2-dimethyl-3-[2- methoxy-2-methoxycarbonyl-ethenyl]-cyclopropane-carboxylate with a specific rotation of $[\alpha]_D^{20} = +3.5°$ (c=1% in chloroform).

NMR Spectrum (deuterochloroform):

Peaks at 1.16–1.3 ppm (hydrogens of geminal methyls); at 1.48–1.57 ppm (1-hydrogen of cyclopropyl); at 2.67–2.76 ppm and 2.8–2.89 ppm (3-hydrogen of cyclopropyl); at 3.58–3.8 ppm (hydrogens of methoxys); at 4.9–5.03 ppm (ethylenic hydrogen); at 5.1 ppm (hydrogen of benzyl methylene); at 6.8 to 7.6 ppm (hydrogens of aromatic ring).

EXAMPLE 3

Using the procedure of Example 2, (S)α-cyano-3-phenoxy-benzyl alcohol was reacted to obtain (S)α-cyano-3-phenoxy-benzyl (1R,trans,ΔZ) 2,2-dimethyl-3-[2-methoxy-2-methoxycarbonyl-ethenyl]-cyclopropane-carboxylate with a specific rotation of $[\alpha]_D^{20} = +7.5°$ (c=0.8% in chloroform).

NMR Spectrum (deuterochloroform):

Peaks at 1.22–1.27 ppm (hydrogens of geminal methyls); at 1.7–1.8 ppm and 2.4 to 2.7 ppm (1- and 3-hydrogens of cyclopropyl); at 3.7–3.8 ppm (hydrogens of methoxys); at 5.9–6.0 ppm (ethylenic hydrogen); at 6.4 ppm (hydrogen of carbon attached to —CN); at 7.0–7.6 ppm (aromatic hydrogens).

EXAMPLE 4

Using the procedure of Example 2, there was obtained 3-phenoxy-benzyl (1R,trans,ΔZ) 2,2-dimethyl-3-[2-methoxy-2-methoxycarbonyl-ethenyl]-cyclopropane-carboxylate with a specific rotation of $[\alpha]_D^{20} = +10°$ (c=0.5% in chloroform).

NMR Spectrum (deuterochloroform):

Peaks at 1.22–1.3 ppm (hydrogens of geminal methyls); at 1.6–1.7 ppm (1-hydrogen of cyclopropyl); at 2.36–2.6 ppm (3-hydrogen of cyclopropyl); at 3.7–3.8 ppm (hydrogens of methoxys); at 5.1 ppm (hydrogens of benzyl methylene); at 6.9–7.6 ppm (aromatic hydrogens); at 5.9–6.1 ppm (ethylenic hydrogen).

EXAMPLE 5

Using the procedure of Example 2, there was obtained 3-allyl-2-methyl-4-oxo-2-cyclopenten-1-yl (1R,trans,ΔE) 2,2-dimethyl-3-[2-methoxy-2-methoxycarbonyl-ethenyl]-cyclopropane-carboxylate melting at 62° C. and having a specific rotation of $[\alpha]_D^{20} = -9.5°$ (c=0.5% in chloroform).

NMR Spectrum (deuterochloroform):

Peaks at 1.18–1.32 ppm (hydrogens of geminal methyls); at 1.45–1.54 ppm (1-hydrogen of cyclopropyl); at 2.06 ppm (hydrogens of 2-methyl of allethrolone; at 2.7–3.0 ppm (3-hydrogen of cyclopropyl); at 3.6–3.8 ppm (hydrogens of methoxys).

EXAMPLE 6

Using the procedure of Example 2, there was obtained 3-allyl-2-methyl-4-oxo-2-cyclopenten-1-yl (1R,trans,ΔZ) 2,2-dimethyl-3-[2-methoxy-2-methoxycarbonyl-ethenyl]-cyclopropane-carboxylate with a specific rotation of $[\alpha]_D^{20} = -5.5°$ (c=0.5% in chloroform):

NMR Spectrum (deuterochloroform):

Peaks at 1.25–1.32 ppm (hydrogens of geminal methyls); at 1.68–1.77 ppm (1-hydrogen of cyclopropyl); at 2.05 ppm (hydrogens of 2-methyl of allethrolone); at 3.74–3.82 ppm (hydrogens of methoxys); at 4.8–5.25 ppm (hydrogens of 3-CH₂ of allyl); at 5.5–6.2 ppm (2-hydrogen of allethrolone); 5.5–6.2 ppm (1-hydrogen of allethrolone); at 5.9–6.1 ppm (ethylenic hydrogen).

EXAMPLE 7

Using the procedure of Example 2, there was obtained (3-propyn-2-yl)-2,5-dioxo-imidazolidinylmethyl (1R,trans,ΔZ) 2,2-dimethyl-3-[2-methoxy-2-methoxycarbonyl-ethenyl]-cyclopropane-carboxylate with a specific rotation of $[\alpha]_D^{20} = +3.5°$ (c=0.5% in chloroform).

NMR Spectrum (deuterochloroform):

Peaks at 1.2–1.3 ppm (hydrogens of geminal methyls); at 1.6–1.7 ppm (1-hydrogen of cyclopropyl); at 2.3–2.4–2.45 ppm (hydrogen of —C≡CH); at 2.35–2.45–2.5–2.6 ppm (3-hydrogen of cyclopropyl); at 3.7–3.8 ppm (hydrogens of methoxys); at 4.05 ppm (hydrogens of imidazolinic methylene); at 5.4–5.55–5.6–5.7 ppm

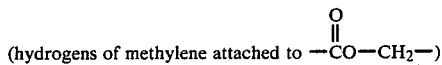

(hydrogens of methylene attached to —CO—CH₂—)

at 4.25–4.30 ppm (hydrogens of methylene of-propynyl).

EXAMPLE 8

Using the procedure of Example 2, there was obtained (S)α-cyano-3-phenoxy-4-fluoro-benzyl (1R,trans,ΔE) 2,2-dimethyl-3-[2-methoxy-2-methoxycarbonyl-ethenyl]-cyclopropane-carboxylate with a specific rotation of $[\alpha]_D^{20} = +3°$ (c=1.5% in chloroform).

NMR Spectrum (deuterochloroform):

Peaks at 1.16–1.25 ppm (hydrogens of geminal methyls); at 1.45–1.55 ppm (1-hydrogen of cyclopropyl); at 2.7–2.9 ppm (3-hydrogen of cyclopropyl); at 3.6–3.8 ppm (hydrogens of methoxys); at 6.4 ppm (hydrogen on carbon attached to —CN); at 6.9–7.6 ppm (aromatic hydrogens).

EXAMPLE 9

Using the procedure of Example 2, there was obtained (S)α-cyano-3-phenoxy-4-fluoro-benzyl (1R,trans,ΔZ) 2,2-dimethyl-3-(2-methoxy-2-methoxycarbonyl-ethenyl]-cyclopropane-carboxylate with a specific rotation of $[\alpha]_D^{20} = +9.5°$ (c=1.2% in chloroform).

NMR Spectrum (deuterochloroform):

Peaks at 1.22–1.25 ppm (hydrogens of geminal methyls); at 1.69–1.78 ppm (1-hydrogen of cyclopropyl); at 2.4–2.66 ppm (3-hydrogen of cyclopropyl); at 2.75–3.82 ppm (hydrogens of methoxys); at 5.9–6.06 ppm (ethylenic hydrogen); at 6.4 ppm (hydrogen of carbon attached to —CN); at 7–7.6 ppm (aromatic hydrogens).

EXAMPLE 10

Using the procedure of Example 2, there was obtained (R,S) -cyano-6-phenoxy-2-pyridylmethyl (1R,trans,ΔE) 2,2-dimethyl-3-[2-methoxy-2-methoxycarbonyl-ethenyl]-cyclopropane-carboxylate with a specific rotation of $[\alpha]_D^{20} = +6°$ (c=0.5% in chloroform).

NMR Spectrum (deuterochloroform):

Peaks at 1.18–1.2–1.28–1.35 ppm (hydrogens of geminal methyls); at 1.52–1.60 ppm (1-hydrogen of cyclopropyl); at 2.68–3.0 ppm (3-hydrogen of cyclopropyl); at 3.6–3.78–3.8 ppm (hydrogens of methoxys); at 4.9–5.0 ppm (ethylenic hydrogen); at 6.4 ppm (hydrogen on carbon attached to —CN); at 6.8–6.96–7–7.7 ppm (3- and 5-hydrogens of pyridine); at 7.65–7.76–7.88 ppm (4-hydrogen of pyridine).

EXAMPLE 11

Using the procedure of Example 2, there was obtained (R,S) -cyano-6-phenoxy-2-pyridylmethyl (1R,trans,ΔZ) 2,2-dimethyl-3-[2-methoxy-2-methoxycarbonyl-ethenyl]-cyclopropane-carboxylate with a specific rotation of $[\alpha]_D^{20} = +13.5°$ (c=0.7% in chloroform).

NMR Spectrum (deuterochloroform):

Peaks at 1.25–1.28–1.35 ppm (hydrogens of geminal methyls); at 1.73–1.82 ppm (1-hydrogen of cyclopropyl); at 2.4–2.67 ppm (3-hydrogen of cyclopropyl); at 3.57–3.77–3.8 ppm (hydrogens of methoxys); at 5.9–6.08 ppm (ethylenic hydrogen); at 6.38 ppm (hydrogen on carbon attached to —CN); at 6.9–8 ppm (aromatic hydrogens).

EXAMPLE 12

Using the procedure of Example 2, there was obtained benzyl (1R,trans,ΔZ) 2,2-dimethyl-3-[2-methoxy-2-methoxycarbonyl-ethenyl]-cyclopropane-carboxylate.

NMR Spectrum (deuterochloroform):

Peaks at 1.22–1.3 ppm (hydrogens of geminal methyls); at 1.7–1.8 ppm (1-hydrogen of cyclopropyl); at 2.37–2.5 ppm (3-hydrogen of cyclopropyl); at 3.7–3.8 ppm (hydrogens of methoxys); at 5.15 ppm (hydrogens of benzyl methylene); at 5.9–6.06 ppm (ethylenic hydrogen); at 7.38 ppm (aromatic hydrogens).

EXAMPLE 13

Using the procedure of Example 2, there was obtained pentafluorobenzyl (1R,trans,ΔZ) 2,2-dimethyl-3-[2-methoxy-2-methoxycarbonyl-ethenyl]-cyclopropane-carboxylate.

NMR Spectrum (deuterochloroform):

Peaks at 1.22–1.32 ppm (hydrogens of geminal methyls); at 1.65–1.74 ppm (1-hydrogen of cyclopropyl); at 2.37–2.61 ppm (3-hydrogen of cyclopropyl); at 3.7–3.8 ppm (hydrogens of methoxys); at 5.22–5.25–5.27 ppm (hydrogens of benzyl —CH2—); at 5.9–6.06 ppm (ethylenic hydrogen).

EXAMPLE 14

Using the procedures of Example 2, there was obtained [1-(3-propyn-2-yl)-2,5-dioxo-imidazolidinyl]-methyl (1R,trans,ΔE) 2,2-dimethyl-3-[2-methoxy-2-methoxycarbonyl-ethenyl]-cyclopropane-carboxylate with a specific rotation of $[\alpha]_D^{20} = 0°$ (c=chloroform).

NMR Spectrum (deuterochloroform):

Peaks at 1.15–1.32 ppm (hydrogens of geminal methyls); at 1.4–1.5 ppm (1-hydrogen of cyclopropyl); at 2.3–2.4–2.43 ppm (hydrogen of ethynyl); at 2.65–2.87 ppm (3-hydrogen of cyclopropyl); at 3.6–3.8 ppm (hydrogens of methoxys); at 4.28–4.32 ppm (hydrogens of —CH2— of propynyl); at 4.9–5.03 ppm (ethylenic hydrogen); at 5.4–5.6–5.62–5.78 ppm

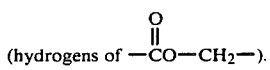
(hydrogens of —CO—CH2—).

EXAMPLE 15

(S)α-cyano-3-phenoxy-benzyl (1R,cis,ΔE and ΔZ) 2,2-dimethyl -3-[2-methoxy-2-methoxycarbonyl-ethenyl]-cyclopropane-carboxylate STEP A: (1R,cis,ΔE and ΔZ) 2,2-dimethyl-3-[2-methoxy-2-methoxycarbonyl-ethenyl]-cyclopropane-carboxylic acid A solution of 4.5 g of potassium tert.-butylate in 30 ml of tetrahydrofuran was added at −45° C. to a solution of 4.24 g of 0,0-dimethylphosphonate of methyl 1-methoxy-acetate, 2.84 g of 1R,5S 6,6-dimethyl-4-(R)-hydroxy-3-oxo-bicyclo [3,1,0]hexane-2-one and 70 ml of tetrahydrofuran and the mixture was stirred at −40° C. for 5 hours and was poured into iced water. The pH was adjusted to 5 by addition of aqueous N hydrochloric acid and the mixture was extracted with ether. The organic phase was evaporated to dryness under reduced pressure to obtain 4.2 g of (1R,cis,ΔE and ΔZ) 2,2-dimethyl-3-[2-methoxy-2-methoxycarbonyl-ethenyl]-cyclopropane-carboxylic acid.

NMR Spectrum (deuterochloroform):

Peaks at 1.29–1.33 ppm (hydrogens of geminal methyls); at 1.76–1.9 ppm (E isomer) and 1.8–1.96 ppm (Z isomer) (1-hydrogen of cyclopropyl); at 2.2–2.5 ppm (Z isomer) and 2.75–3.05 ppm (E isomer) (3-hydrogen of cyclopropyl); at 3.63–3.73 ppm and 3.8–3.05 ppm (hydrogens of methoxys); at 6.55–6.7 ppm (Z isomer) and 5.58–5.73 ppm (E isomer) (ethylenic hydrogen).

STEP B:

Using the procedure of Example 2, the acid of Step A and (S)α-cyano-3-phenoxy-benzyl alcohol were reacted to obtain after chromatography over silica gel and elution with an 8-2 hexane-ethyl acetate mixture (S)α-cyano-3-phenoxy-benzyl (1R,cis,ΔE) 2,2-dimethyl-3-[2-methoxy-2-methoxycarbonyl-ethenyl]-cyclopropane-carboxylate with a specific rotation of $[\alpha]_D^{20} = +7°$ (c=0.3% in chloroform) and the corresponding Z isomer with a specific rotation of $[\alpha]_D^{20} = +29.5°$ (c=0.5% in chloroform).

NMR Spectrum (deuterochloroform):

E isomer:

Peaks at 1.21–1.27 ppm (hydrogens of geminal methyls); at 1.83–1.97 ppm (1-hydrogen of cyclopropyl); at 2.83–3.12 ppm (3-hydrogen of cyclopropyl); at 3.67–3.88 ppm (hydrogens of methoxys); at 5.53–5.68 ppm (ethylenic hydrogen); at 6.4 ppm (hydrogen of carbon attached to —CN); at 7–7.6 ppm (aromatic hydrogens).

Z isomer:

Peaks at 1.26 ppm (hydrogens of geminal methyls); at 1.89–2.03 ppm (1-hydrogen of cyclopropyl); at 1.28–2.6 ppm (3-hydrogen of cyclopropyl); at 3.75–3.81 ppm (hydrogens of methoxys); at 6.5 ppm (hydrogen of carbon attached to —CN); at 6.5–6.7 ppm (ethylenic hydrogen); at 6.98–7.7 ppm (aromatic hydrogens).

EXAMPLE 16

(S)α-cyano-3-phenoxy-benzyl (1R,trans,ΔZ) 2,2-dimethyl-3-[2-methoxy-2-isopropoxycarbonyl-ethenyl]-cyclopropane-carboxylate STEP A: Methoxymethyl (1R,trans,ΔZ and ΔE) 2,2-dimethyl-3-[2-methoxy-2-isopropoxycarbonyl-ethenyl]-cyclopropane-carboxylate 2.75 ml of a solution of 20% butyllithium in cyclohexane were added at −60° C. to a mixture of 1.66 g of 1-isopropoxycarbonyl-1-methoxymethyl-diphenyl-phosphine oxide in 60 ml of tetrahydrofuran and then a solution of 930 mg of methoxymethyl 2,2-dimethyl-3-formyl-cyclopropane-carboxylate in 10 ml of tetrahydrofuran were added thereto. The mixture was stirred at −60° C. for 6 hours and was poured into water. The mixture was extracted with ether and the organic phase was evaporated to dryness under reduced pressure. The residue was chromatographed over silica gel and was eluted with an 8-2 hexane-ethyl acetate mixture to obtain 650 mg of methoxymethyl (1R,trans,ΔZ) 2,2-dimethyl-3-[2-methoxy-2-isopropoxycarbonyl-ethenyl]-cyclopropane-carboxylate and 380 mg of the E isomer.

NMR Spectrum (deuterochloroform):
Z isomer:
Peaks at 1.25-1.33 ppm (hydrogens of geminal methyls); at 1.31-1.35 ppm (hydrogens of methyls of isopropyl); at 1.7-1.80 ppm (1-hydrogen of cyclopropyl); at 2.57-2.63 ppm (3-hydrogen of cyclopropyl); at 3.5 ppm (hydrogens of methyl of methoxymethyl); at 3.7 ppm (hydrogens of CH₃O—); at 5.08 ppm

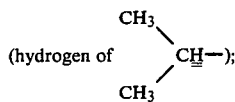

at 5.3 ppm (hydrogens of methylene of methoxymethyl).

E isomer:
Peaks at 1.22-1.35 ppm (hydrogens of geminal methyls); at 1.3-1.42 ppm (hydrogens of methyls of isopropyl); at 1.49-1.58 ppm (1-hydrogen of cyclopropyl); at 2.75-3 ppm (3-hydrogen of cyclopropyl); at 3.6 ppm (hydrogens of CH₃O—); at 3.5 ppm (hydrogens of methyls of methoxymethyl); at 4.88-5.02 ppm (ethylenic hydrogen); at 5.3 ppm (hydrogens of —CH₂— of methoxymethyl).

STEP B: (1R,trans,ΔZ) 2,2-dimethyl-3-[2-methoxy-2-isopropoxycarbonyl-ethenyl]-cyclopropane-carboxylic acid A mixture of 5.4 g of the Z isomer of Step A, 100 ml of methanol, 100 ml of acetone and 200 ml of aqueous N sodium hydroxide solution was stirred at 20° C. for 16 hours and was then poured into water. The mixture was extracted with methylene chloride and the organic phase was evaporated to dryness under reduced pressure to obtain 4.6 g of (1R,trans ΔZ) 2,2-dimethyl-3-[2-methoxy-2-isopropoxycarbonyl-ethenyl]cyclopropane-carboxylic acid.

NMR Spectrum (deuterochloroform):
Peaks at 1.27-1.38 ppm (hydrogens of geminal methyls); at 1.67-1.77 ppm (1-hydrogen of cyclopropyl); at 2.38-2.63 ppm (3-hydrogen of cyclopropyl); at 3.05 ppm (hydrogens of methyls of isopropyl); at 3.76 ppm (hydrogens of CH₃O—); at 5.17 ppm

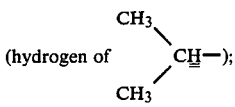

at 5.9-6.08 ppm (ethylenic hydrogen).

STEP C: (S)α-cyano-3-phenoxy-benzyl (1R,trans,ΔZ) 2,2-dimethyl-3-[2-methoxy-2-isopropoxycarbonyl-ethenyl]-cyclopropane-carboxylate Using the procedure of Example 2, the compound of Step B and (S)α-cyano-3-phenoxy-benzyl alcohol were reacted to obtain (S)α-cyano-3-phenoxy-benzyl (1R,trans,ΔZ) 2,2-dimethyl-3-[2-methoxy-2-isopropoxycarbonyl-ethenyl]-cyclopropane-carboxylate with a specific rotation of $[\alpha]_D^{20} = +9.5°$ (c=0.5% in CHCl₃).

NMR Spectrum (deuterochloroform):
Peaks at 1.22-1.27 ppm (hydrogens of geminal methyls); at 1.25-1.35 ppm (hydrogens of methyls of isopropyl); at 1.72-1.77 ppm (1-hydrogen of cyclopropyl); at 2.41-2.67 ppm (3-hydrogen of cyclopropyl); at 3.7 ppm (hydrogens of CH₃O—); at 5.1 ppm

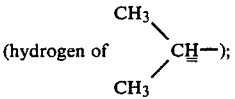

at 5.8 ppm and 5.96 ppm (ethylenic hydrogen); at 6.4 ppm (hydrogen of carbon attached to —CN); at 6.9-7.6 ppm (aromatic hydrogens).

EXAMPLE 17

(S)α-cyano-3-phenoxy-benzyl (1R,trans,ΔZ) 2,2-dimethyl-3-[2-methoxy-2-tert.-butoxycarbonyl-ethenyl]-cyclopropane-carboxylate STEP A: ΔE and ΔZ isomers of methoxymethyl (1R,trans) 2,2-dimethyl-3-[2-methoxy-2-tert.-butoxycarbonyl-ethenyl]-cyclopropane-carboxylate 2.75 ml of a solution of 20% butyllithium in cyclohexane were added at −60° C. to a mixture of 1.73 g of 1-tert.-butoxycarbonyl-1-methoxymethyl-diphenyl-phosphine oxide in 60 ml of tetrahydrofuran and then a solution of 920 mg of methoxymethyl 2,2-dimethyl-3-formyl-cyclopropane-carboxylate in 10 ml of tetrahydrofuran was added thereto. The mixture was stirred at −60° C. for 5 hours and was then poured into water. The mixture was extracted with ether and the organic phase was evaporated to dryness under reduced pressure. The residue was chromatographed over silica gel and was eluted with an 8-2 hexane-ethyl acetate mixture to obtain 0.7 g of the Z isomer of methoxymethyl (1R, trans) 2,2-dimethyl-3-[2-methoxy-2-tert.-butoxycarbonyl-ethenyl]cyclopropane-carboxylate and 0.72 g of the E isomer.

NMR Spectrum (deuterochloroform):
Z isomer:
Peaks at 1.25-1.35 ppm (hydrogens of geminal methyls); at 1.53 ppm (hydrogens of methyls of tert.-butyl); at 1.68-1.77 ppm (1-hydrogen of cyclopropyl); at 2.37-2.6 ppm (3-hydrogen of cyclopropyl); at 3.5 ppm (hydrogens of methyl of methoxymethyl); at 5.3 ppm (hydrogens of —CH₂— of methoxymethyl); at 5.8-6 ppm (ethylenic hydrogen).

E isomer:

Peaks at 1.22–1.34 ppm (hydrogens of geminal methyls); at 1.56 ppm (hydrogens of methyls of tert.-butyl); at 3.5 ppm (hydrogens of methyl of methoxymethyl).

STEP B: (1R,trans,ΔZ)
2,2-dimethyl-3-[2-methoxy-2-tert.-butoxycarbonyl-ethenyl]-cyclopropane-carboxylic acid A mixture of 520 mg of the Z isomer of Step A, 10 ml of methanol, 10 ml of acetone and 20 ml of aqueous N sodium hydroxide was stirred at 20° C. for 16 hours and was poured into water. The mixture was extracted with methylene chloride and the organic phase was evaporated to dryness under reduced pressure to obtain 420 mg of (1R,trans,ΔZ) 2,2-dimethyl-3-[2-methoxy-2-tert.-butoxycarbonyl-ethenyl]-cyclopropane-carboxylic acid.

NMR Spectrum (deuterochloroform):
Peaks at 1.26–1.37 ppm (hydrogens of geminal methyls); at 1.55 ppm (hydrogens of methyls of tert.-butyl); at 1.65–1.74 ppm (1-hydrogen of cyclopropyl); at 2.37–2.6 ppm (3-hydrogen of cyclopropyl); at 3.77 ppm (hydrogens of $CH_3O$—); at 5.87–6.03 ppm (ethylenic hydrogen).

STEP C: (S)α-cyano-3-phenoxy-benzyl (1R,trans,ΔZ) 2,2-dimethyl-3-[2-methoxy-2-tert.-butoxycarbonyl-ethenyl]-cyclopropane-carboxylate Using the procedure of Example 2, the acid of Step B and (S)α-cyano-3-phenoxy-benzyl alcohol were reacted to obtain (S)α-cyano-3-phenoxy-benzyl (1R,trans,ΔZ) 2,2-dimethyl -3-[2-methoxy-2- tert.-butoxycarbonyl-ethenyl]-cyclopropane-carboxylate melting at 66° C. and having a specific rotation of $[\alpha]_D^{20} = +7.5°$ (c=0.5% in chloroform).

NMR Spectrum (deuterochloroform):
Peaks at 1.22 ppm (hydrogens of geminal methyls); at 1.53 ppm (hydrogens of methyls of tert.-butyl); at 1.7–1.79 ppm (1-hydrogen of cyclopropyl); at 2.42–2.66 ppm (3-hydrogen of cyclopropyl); at 3.73 ppm (hydrogens of $CH_3O$—); at 5.8–5.97 ppm (ethylenic hydrogen); at 6.47 ppm (hydrogen of carbon attached to —CN); at 6.9–7.58 ppm (aromatic hydrogens).

EXAMPLE 18

(S)α-cyano-3-phenoxy-benzyl (1R,trans,ΔZ)
2,2-dimethyl-3-[2-methoxy-2-ethoxycarbonyl-ethenyl]-cyclopropane-carboxylate STEP A: Tert.-butyl (1R,trans,ΔZ)
2,2-dimethyl-3-[2-methoxy -2-ethoxycarbonyl-ethenyl]-cyclopropane-carboxylate 0.05 ml of ethanol were added at 0° C. to a mixture of 1.25 g of small pieces of sodium in 25 ml of toluene and then as solution of 9.9 g tert.-butyl 2,2-dimethyl-3-formylcyclopropane-carboxylate in 17.7 g of ethyl methoxyacetate was added dropwise thereto. The mixture was stirred at 20° C. for 16 hours and was poured into water. The mixture was extracted with methylene chloride and the organic phase was evaporated to dryness under reduced pressure. The residue was chromatographed over silica gel and was eluted with a hexane-ethyl acetate mixture to obtain 10 g of tert.-butyl (1R,trans,ΔZ) 2,2-dimethyl-3-[2-methoxy-2-ethoxycarbonyl-ethenyl]-cyclopropanecarboxylate.

NMR Spectrum (deuterochloroform):
Peaks at 1.2–1.3 ppm (hydrogens of geminal methyls); at 1.47 ppm (hydrogens of methyls of tert.-butyl); at 1.16–1.28–1.4 ppm and 4.05–4.16–4.28–4,4 ppm (hydrogens of ethyl of ethoxy); at 1.57–1.66 ppm (1-hydrogen of cyclopropyl); at 2.15–2.34 ppm and 2.4–2.5 ppm (3-hydrogen of cyclopropyl); at 3.7 ppm (hydrogens of $CH_3O$—); at 5.86–6.03 ppm (ethylenic hydrogen).

STEP B: (1R,trans,ΔZ)
2,2-dimethyl-3-[2-methoxy-2-ethoxycarbonyl-ethenyl]-cyclopropane-carboxylic acid 0.5 g of p-toluene sulfonic acid was added to a refluxing mixture of 5.6 g of the product of Step A in 60 ml of toluene and the mixture was refluxed for one hour and poured into water. The decanted aqueous phase was extracted with ether and the combined organic phases were evaporated to dryness under reduced pressure. The residue was chromatographed over silica gel and eluted with a 4-6 hexane-ethyl acetate mixture to obtain 3.2 g of (1R,trans,ΔZ) 2,2-dimethyl-3-[2-methoxy-2-ethoxycarbonyl-ethenyl]-cyclopropane-carboxylic acid.

NMR Spectrum (deuterochloroform):
Peaks at 1.25–1.36 ppm (hydrogens of geminal methyls); at 1.2–1.32–1.43 ppm and 4.03–4.15–4.26–4.38 ppm (hydrogens of $CH_3$—$CH_2$—); at 1.65–1.74 ppm (1-hydrogen of cyclopropyl); at 2.35–2.44 ppm and 2.52–2.61 ppm (3-hydrogen of isopropyl); at 3.7 ppm (hydrogens of $CH_3O$—); at 5.66–6.03 ppm (ethylenic hydrogen); at 10.01 ppm (hydrogen of —COOH).

STEP C: (S)α-cyano-3-phenoxy-benzyl (1R,trans,ΔZ)
2,2-dimethyl-3-[2-methoxy-2-ethoxycarbonyl-ethenyl]-cyclopropane-carboxylate Using the procedure of Example 2, the acid of Step B and (S)α-cyano-3-phenoxy-benzyl alcohol were reacted to obtain (S)α-cyano-3-phenoxy-benzyl (1R,trans,ΔZ) 2,2-dimethyl-3-[2-methoxy-2-ethoxycarbonyl-ethenyl]-cyclopropane-carboxylate.

NMR Spectrum (deuterochloroform):
Peaks at 1.21–1.26 ppm (hydrogens of geminal methyls); at 1.2–1.3–1.4 ppm and 4.1–4.2–4.3–4.4 ppm (hydrogens of $CH_3$—$CH_2$—); at 1.7–1.8 ppm and 2.43–2.5–2.6–2.7 ppm and (1-and 3-hydrogens of cyclopropyl); at 3.74 ppm (hydrogens of $CH_3O$—); at 5.09–6.05 ppm (ethylenic hydrogen); at 6.43 ppm (hydrogen of carbon attached to —CN).

EXAMPLE 19

(S)α-cyano-3-phenoxy-benzyl (1R,trans, Z)
2,2-dimethyl-3-[2-ethoxy-2-ethoxycarbonyl-ethenyl]-cyclopropane-carboxylate STEP A: E and Z isomers of tert.-butyl (1R,trans)
2,2-dimethyl-3-[2-ethoxy-2-ethoxycarbonyl-ethenyl]-cyclopropane-carboxylate A solution of 10.5 ml of butyllithium in cyclohexane (titrating 2 moles per liter) was slowly added at −60° C. to a solution of 5.36 g of 0,0-diethyl 1-ethoxy-1-ethoxycarbonylmethyl phosphonate in 40 ml of tetrahydrofuran and after stirring the mixture for 10 minutes, 3.96 g of tert.-butyl 2,2-dimethyl-3-formyl-cyclopropane-carboxylate were added thereto at −60° C. The mixture was stirred at −60° C. for 5 hours and was poured into water. The mixture was extracted with ether and the organic phase was evaporated to dryness under reduced pressure. The residue was chromatographed over silica gel and was eluted with a 9-1 hexane-ethyl acetate mixture to obtain 1.35 g of the Z isomer of tert.-butyl (1R, trans)     2,2-dimethyl-3-[2-ethoxy-2-ethoxycarbonylethenyl]-cyclopropane-carboxylate and 3.46 of the E isomer.

NMR Spectrum (deuterochloroform):

Z isomer:

Peaks at 1.2–1.3 ppm (hydrogens of geminal methyls); at 1.18–1.43 ppm and 3.75–4.1 ppm (hydrogen of CH$_3$—CH$_2$O) at 1.18–1.43 ppm and 4.06–4.43 ppm

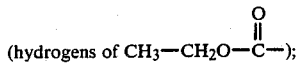

at 1.47 ppm (hydrogens of methyls of tert.-butyl); at 1.57–166 ppm (1-hydrogen of cyclopropyl); at 2.27–2.36 ppm and 2.44–2.53 ppm (3-hydrogen of cyclopropyl); at 5.95–6.61 ppm (ethylenic hydrogen).

E isomer:

Peaks at 1.06–1.28 ppm (hydrogens of geminal methyls); at 1.22–1.33–1.45 ppm and 3.6–3.7–3.8–3.9 ppm (hydrogens of CH$_3$—CH$_2$O—); at 1.22–1.33–1.45 ppm and 4.1-4-2–4.3–4.4 ppm

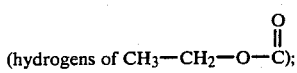

at 1.15–1.47 ppm (1-hydrogen of cyclopropyl); at 1.47 ppm (hydrogen of methyls of tert.-butyl); at 2.53–2.62 ppm (and 2.67–2.76 ppm (3-hydrogen of cyclopropyl); at 4.54–5.08 ppm (ethylenic hydrogen).

STEP B: (1R,trans,ΔZ) 2,2-dimethyl-3-[2-ethoxy-2-ethoxycarbonyl)-ethenyl]-cyclopropane-carboxylic acid A mixture of 0.32 g of p-toluene sulfonic acid, 3.2 g of the Z isomer of Step A and 32 ml of toluene was refluxed for 45 minutes and was then evaporated to dryness under reduced pressure. The residue was added to ether and the solution was washed with water and evaporated to dryness under reduced pressure. The residue was chromatographed over silica gel and eluted with a 4-6 hexane-ethyl acetate mixture to obtain 1.84 g of (1R,trans,ΔZ) 2,2-dimethyl-3-[2-ethoxy-2-ethoxycarbonyl)-ethenyl]-cyclopropane-carboxylic acid.

NMR: Spectrum (deuterochloroform):

Peaks at 1.25–1.35 ppm (hydrogens of geminal methyls); at 1.2–1.3–1.4 ppm and 3.76–3.88–4.0–4.1 ppm (hydrogens of CH$_3$—CH$_2$O—); at 1.2–1.3–1.4 ppm and 4.08–4.2–4.3–4.4 ppm

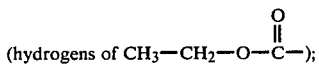

at 1.65–1.75 ppm (1-hydrogen of cyclopropyl); at 2.4–2.49–2.56–2.65 ppm (3-hydrogen of cyclopropyl); at 5.95–6.11 ppm (ethylenic hydrogen); at 7.33 ppm (hydrogen of —COOH).

STEP C: (S)α-cyano-3-phenoxy-benzyl (1R,trans,ΔZ) 2,2-dimethyl-3-[2-ethoxy-2-ethoxycarbonyl-ethenyl]-cyclopropane-carboxylate Using the procedure of Example 2, the acid of Step B and (S)α-cyano-3-phenoxy-benzyl alcohol were reacted to obtain (S)α-cyano-3-phenoxy-benzyl (1R,trans,ΔZ) 2,2-dimethyl-3-[2-ethoxy-2-ethoxycarbonyl-ethenyl]-cyclopropane-carboxylate.

NMR Spectrum (deuterochloroform):

Peaks at 1.2–1.95 ppm (hydrogens of geminal methyls); at 1.15–1.17–1.38 ppm and 3.75–3.87–3.98–4.1 ppm (hydrogens of CH$_3$—CH$_2$O—); at 1.15–1.17–1.38 ppm and 4.05–4.16–4.23–4.4 ppm

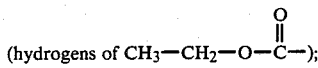

at 1.7–1.8 ppm (1-hydrogen of cyclopropyl); at 2.4–2.68 ppm (3-hydrogen of cyclopropyl); at 5.9–6.0 ppm (ethylenic hydrogen); at 6.38 ppm (hydrogen of carbon attached to —CN); at 6.9–7.5 ppm (aromatic hydrogens).

EXAMPLE 20

(S)α-cyano-3-phenoxy-benzyl (1R,trans,ΔE) 2,2-dimethyl-3-[2-ethoxy-2-ethoxycarbonyl-ethenyl]-cyclopropane-carboxylate

STEP A: (1R,trans,ΔE) 2,2-dimethyl-3-[2-ethoxy-2-ethoxycarbonyl-ethenyl]-cyclopropane-carboxylic acid 13.4 ml of trifluoroacetic acid were added at 0° C. to a solution of 3.38 g of tert.-butyl (1R,trans,ΔE) 2,2-dimethyl-3-[2-ethoxy-2-ethoxycarbonyl-ethenyl]-cyclopropane-carboxylate in 70 ml of methylene chloride and the mixture was stirred at 0° C. for 3 hours after which cyclohexane was added. The mixture was evaporated to dryness under reduced pressure and the residue was chromatographed over silica gel. Elution with a 4-6 hexane-ethyl acetate mixture yield 1.81 g of (1R,trans,ΔE) 2,2-dimethyl-3-[2-ethoxy-2-ethoxycarbonyl-ethenyl]-cyclopropane-carboxylic acid.

NMR Spectrum (deuterochloroform):

Peaks at 1.19–1.35 ppm (hydrogens of geminal methyls); at 1.23–1.35–1.46 ppm and 4.15–4.26–4.38–4.5 ppm

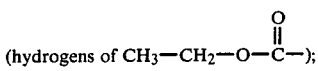

at 1.23–1.35–1.46 ppm and 3.6–3.7–3.8–3.95 ppm (hydrogens of CH$_3$—CH$_2$—O—); at 1.43–1.52 ppm (1-hydrogen of cyclopropyl); at 2.8–2.9–2.69–2.78 ppm (3-hydrogen of cyclopropyl); at 4.96–5.1 ppm (ethylenic hydrogen); at 9 ppm (hydrogen of —COOH).

STEP B: (S)α-cyano-3-phenoxy-benzyl (1R,trans,ΔE) 2,2-dimethyl-3-[2-ethoxy-2-ethoxycarbonyl-ethenyl]-cyclopropane-carboxylate Using the procedure of Example 1, the acid of Step A and (S)α-cyano-3-phenoxy-benzyl alcohol were reacted to obtain (S)α-cyano-3-phenoxy-benzyl (1R,trans,ΔE) 2,2-dimethyl-3-[2-ethoxy-2-ethoxycarbonyl-ethenyl]-cyclopropane-carboxylate with a specific rotation of $[\alpha]_D^{20} = +9.5°$ (c=1% in CHCl$_3$).

NMR Spectrum (deuterochloroform):

Peaks at 1.15–1.25 ppm (hydrogens of geminal methyls); at 1.2–1.45 ppm and 4.15–4.26–4.38–4.5 ppm

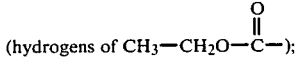

at 1.2–1.45 ppm and 3.6–3.7–3.8–3.95 ppm (hydrogens of CH$_3$—CH$_2$O—); at 1.49–1.58 ppm (1-hydrogen of cyclopropyl); at 2.7-2.8-2.85-2.95 ppm (3-hydrogen of cyclopropyl); at 4.9-5.0 ppm (aromatic hydrogen); at 6.43 ppm (hydrogen of carbon attached to —CN); at 6.9-7.6 ppm (aromatic hydrogens).

EXAMPLE 21

(S)α-cyano-3-phenoxy-benzyl (1R,trans,ΔE or ΔZ) 2,2-dimethyl-3-[2-phenoxy-2-ethoxycarbonyl-ethenyl]-cyclopropane-carboxylate STEP A: E or Z isomer of tert.-butyl (1R,trans) 2,2-dimethyl-3-[2-phenoxy-2-ethoxycarbonyl-ethenyl]-cyclopropane-carboxylate 9.9 g of tert.-butyl 2,2-dimethyl-3-formyl-cyclopropane-carboxylate and 28 g of ethyl phenoxyacetate were added dropwise at 0° C. to a mixture of 0.05 ml of ethanol, 1.25 g of sodium in small pieces and 25 ml of toluene and the solution was stirred at 20° C. for 16 hours. 20 ml of toluene were added thereto and the mixture was stirred for 4 hours and was poured into iced water. The mixture was extracted with methylene chloride and the organic phase was evaporated to dryness under reduced pressure. The residue was chromatographed over silica gel and was eluted with a 7-3 hexane-ethyl acetate mixture to obtain 12.47 g of E or Z isomer of tert.-butyl (1R,trans) 2,2-dimethyl-3-[2-phenoxy-2-ethoxycarbonyl-ethenyl]-cyclopropane-carboxylate.

NMR Spectrum (deuterochloroform):
Peaks at 1.05-1.16-1.28 ppm and 3.96-4.08-4.2-4.3 ppm (hydrogens of CH$_3$—CH$_2$—); at 1.15-1.23 ppm (hydrogens of geminal methyls); at 1.37 ppm (hydrogens of methyls of tert.-butyl); at 1.62-1.70 ppm (1-hydrogen of cyclopropyl); at 2.13-2.4 ppm (3-hydrogen of cyclopropyl); at 6.23-6.4 ppm (ethylenic hydrogen); at 6.7-7.4 ppm (aromatic hydrogens).

STEP B: (1R,trans,ΔE or ΔZ) 2,2-dimethyl-3-[2-phenoxy-2-ethoxycarbonyl-ethenyl]-cyclopropane-carboxylic acid 1 g of p-toluene-sulfonic acid was added to a refluxing mixture of 12 g of the product of Step A in 120 ml of toluene and after refluxing for one hour, the mixture was poured into water. The decanted organic phase was evaporated to dryness under reduced pressure and the residue was chromatographed over silica gel. Elution with a 4-6 hexane-ethyl acetate mixture yielded 7.91 g of (1R,trans,ΔE or ΔZ) 2,2-dimethyl-3-[2-phenoxy-2-ethoxycarbonyl-ethenyl]-cyclopropane-carboxylic acid.

IR Spectrum (chloroform):
Absorption at 3510 cm$^{-1}$ (mono and dimeric acid —OH); 1720 cm$^{-1}$ (carbonyl of ester); at 1699 cm$^{-1}$ (dimeric acid); at 1655 cm$^{-1}$ (shoulder) and 1651 cm$^{-1}$ maximum (conjugated C=C); at 1600, 1594, 1491 cm$^{-1}$ (aromatic); at 1380 cm$^{-1}$ (geminal methyls).

STEP C: E or Z isomer of (S)α-cyano-3-phenoxy-benzyl (1R, trans) 2,2-dimethyl-3-[2-phenoxy-2-ethoxycarbonyl-ethenyl]-cyclopropane-carboxylate Using the procedure of Example 2, the acid of Step B and (S)α-cyano-3-phenoxy-benzyl alcohol were reacted to obtain E or Z isomer of (S)Δ-cyano-3-phenoxy-benzyl (1R,trans) 2,2-dimethyl-3-[2-phenoxy-2-ethoxycarbonyl-ethenyl]-cyclopropane-carboxylate.

NMR Spectrum (deuterochloroform):
Peaks at 1.06-1.18-1.3 ppm and 4.01-4.13-4.25-4.37 ppm (hydrogens of ethyl); at 1.13-1.15 ppm (hydrogens of geminal methyls); at 1.8-1.9 ppm (1-hydrogen of cyclopropyl); at 2.3-2.4-2.46-2.55 ppm (3-hydrogen of cyclopropyl); at 6.27-6.46 ppm (ethylenic hydrogen); at 6.36 ppm (hydrogen of carbon attached to —CN).

EXAMPLE 22

(S)α-cyano-2-phenoxy-benzyl (1R,cis,ΔZ) 2,2-dimethyl-3-[2-methylthio-2-ethoxycarbonyl-ethenyl]-cyclopropane-carboxylate STEP A: (1R,cis) 2,2-dimethyl-3-(1-hydroxy-2-methylthio-2-ethoxycarbonyl-ethyl]-cyclopropane-carboxylic acid A solution of 18 g of potassium tert.-butylate in 140 ml of tetrahydrofuran was added over 30 minutes at −60° C. to a mixture of 11.54 g of ethyl methylthioacetate, 11.36 g of 1R,5S 6,6-dimethyl-4-(R)-hydroxy-3-oxa-bicyclo [3,1,0] hexane-2-one and 200 ml of tetrahydrofuran and the mixture was stirred at −60° C. for one hour. 200 ml of N hydrochloric acid were added to the mixture over 10 minutes at less than −20° C. and the mixture was poured into 1.5 liters of water. The mixture was extracted with methylene chloride and the organic phase was evaporated to dryness under reduced pressure and the residue was crystallized from isopropyl ether to obtain 10.22 g of (1R,cis) 2,2-dimethyl-3-(1-hydroxy-2-methylthio-2-ethoxycarbonyl-ethenyl]-cyclopropane-carboxylic acid melting at 114° C.

STEP B: 6,6-dimethyl-4-[methylthio-ethoxycarbonyl-methyl]-3-oxa-bicyclo [3,1,0]-hexane-2-one A mixture of 9.67 g of the product of Step A, 80 mg of p-toluene sulfonic acid and 120 ml of benzene was refluxed and 60 ml of benzene were distilled over 90 minutes equipped with a flask of Dean Stark apparatus containing silica gel. The mixture was evaporated to dryness under reduced pressure and the residue was chromatographed over silica gel. Elution with a 6-4 hexane-ethyl acetate mixture yielded 7.36 of 6,6-dimethyl-4-[methylthio-ethoxycarbonyl-methyl]-3-oxa-bicyclo [3,1,0]-hexane-2-one.

STEP C: Z and E isomers of (1R,cis) 2,2-dimethyl-3-[2-methylthio-2-ethoxycarbonyl-ethenyl]-cyclopropane-carboxylic acid A mixture of 6.5 g of the product of Step A, 6 ml of triethylamine and 60 ml of benzene was refluxed for 3 hours and was cooled and poured into 100 ml of 2N hydrochloric acid with stirring. The decanted organic phase was evaporated to dryness and the residue was chromatographed over silica gel. Elution with a 8-2 methylene chloride-ethyl acetate mixture yielded 2.5 g of the Z isomer and 170 mg of the E isomer and 1.74 g of a mixture of E and Z isomers. The latter mixture was chromatographed over silica gel and eluted with a 9-1 methylene chloride-ethyl acetate mixture to obtain 220 mg of the E isomer.

NMR Spectrum (deuterochloroform):
E isomer:
Peaks at 1.2-1.3-1.4 ppm and 4.1-4.2-4.4-4.5 ppm (hydrogens of ethyl); at 1.27-1.35 ppm (hydrogens of geminal methyls); at 1.8-1.9-2.8-2.9-3.1 ppm (1- and 3-hydrogens of cyclopropyl); at 2.2 ppm (hydrogens of CH$_3$S—); at 6.25-6.41 ppm (ethylenic hydrogen).
Z isomer:

Peaks at 1.2–1.3–1.4 ppm and 4.1–4.2–4.3–4.5 ppm (hydrogens of ethyl); at 1.3–1.36 ppm (hydrogens of geminal methyls); at 1.9–2.05 ppm and 2.5–2.6–2.8 ppm (1- and 3-hydrogens of cyclopropyl); at 2.3 ppm (hydrogens of CH$_3$—S—); at 6.5 ppm (hydrogen of —COOH); at 7.4–7.6 ppm (ethylenic hydrogen).

STEP D: (S)α-cyano-3-phenoxy-benzyl (1R,cis,ΔZ) 2,2-dimethyl-3-[2-methylthio-2-ethoxycarbonyl-ethenyl]-cyclopropane-carboxylate Using the procedure of Example 2, the Z isomer of the acid of Step C and (S)α-cyano-3-phenoxy-benzyl alcohol were reacted to obtain (S)α-cyano-3-phenoxy-benzyl (1R,cis,ΔZ2,2-dimethyl-3-[2-methylthio-2-ethoxycarbony-ethenyl]-cyclopropane-carboxylate.

NMR Spectrum (deuterochloroform):
Peaks at 1.22–1.33–1.45 ppm and 4.13–4.25–4.37–4.48 ppm (hydrogens of ethyl); at 1.25–1.28 ppm (hydrogens of geminal methyls); at 1.97–2.10 ppm (1-hydrogen of cyclopropyl); at 2.55–2.65–2.74–2.85 ppm (3-hydrogen of cyclopropyl); at 6.46 ppm (hydrogen on carbon attached —CN); at 7.0–7.67 ppm (aromatic hydrogens).

EXAMPLE 23

(S)α-cyano-3-phenoxy-benzyl (1R,trans,ΔZ) 2,2-dimethyl-3-[2-methylthio-2-ethoxycarbonyl-ethenyl]-cyclopropane-carboxylate

STEP A: Tert.-butyl (1R,trans,ΔZ) 2,2-dimethyl-3-[2-methylthio-2-ethoxycarbonyl-ethenyl]-cyclopropane-carboxylate 2.3 g of sodium were added at 0° C. to 50 ml of ethanol and the sodium ethanolate and 9.9 g of tert.-butyl 2,2-dimethyl-3-formyl-cyclopropane-carboxylate and 13.4 g of ethyl methylthioacetate were admixed with stirring at 5° C. for 16 hours. The mixture was evaporated to dryness under reduced pressure and the residue was added to a stirred water-ether mixture. The decanted organic phase was washed with water and evaporated to dryness under reduced pressure. The residue was chromatographed over silica gel and eluted with an 8-2 hexane-ethyl acetate mixture to obtain 5.6 g of tert.-butyl (1R,trans,ΔZ) 2,2-dimethyl-3-[2-methylthio-2-ethoxycarbonylethenyl]-cyclopropane-carboxylate.

NMR Spectrum (deuterochloroform):
Peaks at 1.15–1.27–1.38 ppm and 4.05–4.16–4.28–4.4 ppm (hydrogens of ethyl); at 1.18–1.27 ppm (hydrogens of geminal methyls); at 1.43 ppm (hydrogens of methyls of tert.-butyl); at 1.67–1.75 ppm (1-hydrogen of cyclopropyl); at 2.28 ppm (hydrogens of CH$_3$S—); at 2.53–2.78 ppm (3-hydrogen of cyclopropyl); at 6.7–6.8 ppm (ethylenic hydrogen).

STEP B: (1R,trans,ΔZ) 2,2-dimethyl-3-[2-methylthio-2-ethoxycarbonyl-ethenyl]-cyclopropane-carboxylic acid A mixture of 5 g of the product of Step A, 0.5 g of p-toluene sulfonic acid and 50 ml of toluene was refluxed for 45 minutes, was cooled to 20° C. and poured into 100 ml of water. The mixture was extracted with ether and the combined organic phases were dried and evaporated to dryness under reduced pressure. The residue was chromatographed over silica gel and was eluted with a 4-6 hexane-ethyl acetate mixture to obtain 3.47 g of (1R,trans,ΔZ) 2,2-dimethyl-3-[2-methylthio-2-ethoxycarbonyl-ethenyl]-cyclopropane-carboxylic acid.

NMR Spectrum (deuterochloroform):
Peaks at 1.27–1.38 ppm (hydrogens of geminal methyls); at 2.65–2.74–2.82–2.90 ppm (3-hydrogen of cyclopropyl); at 1.77–1.87 ppm (1-hydrogen of cyclopropyl); at 6.77–6.8 ppm (ethylenic hydrogen); at 2.28 ppm (hydrogens of CH$_3$S); at 1.22–1.33–1.45 ppm and 4.1–4.2–4.3–4.4 ppm (hydrogens of ethyl).

STEP C: (S)α-cyano-3-phenoxy-benzyl (1R,trans,ΔZ) 2,2-dimethyl-3-[2-methylthio-2-ethoxycarbonyl-ethenyl]-cyclopropane-carboxylate Using the procedure of Example 2, the acid of Step B and (S)α-cyano-3-phenoxy-benzyl alcohol were reacted to obtain (S)α-cyano-3-phenoxy-benzyl (1R,trans,ΔZ) 2,2-dimethyl-3-[2-methylthio-2-ethoxycarbonyl-ethenyl]-cyclopropane-carboxylate.

NMR Spectrum (deuterochloroform):
Peaks at 1.23–1.3 ppm (hydrogens of geminal methyls); at 1.8–1.9 ppm (1-hydrogen of cyclopropyl); at 2.3 ppm (hydrogens of CH$_3$S—); at 2.7–2.8–2.9–3.0 ppm (3-hydrogen of cyclopropyl); at 6.5 ppm (hydrogen of carbon attached to —CN); at 6.7–6.9 ppm (ethylenic hydrogen); at 7.0–7.6 ppm (aromatic hydrogens).

EXAMPLE 24

(S)α-cyano-3-phenoxy-benzyl (1R,trans, ΔE or ΔZ) 2,2-dimethyl-3-[2-phenylthio-2-ethoxycarbonyl-ethenyl]-cyclopropane-carboxylate

STEP A: Tert.-butyl (1R,trans, ΔE or ΔZ) 2,2-dimethyl-3-[2-phenylthio-2-ethoxycarbonyl-ethenyl]-cyclopropane-carboxylate A mixture of 9.9 g of tert.-butyl 2,2-dimethyl-3-formyl-cyclopropane-carboxylate and 19.6 g of ethyl phenylthio-acetate were added at 0° C. to a solution of 2.3 g of sodium in 50 ml of ethanol and the mixture was stirred at 5° C. for 16 hours and was evaporated to dryness under reduced pressure. The residue was added to water and ether with stirring and the decanted organic phase was evaporated to dryness under reduced pressure. The residue was chromatographed over silica gel and was eluted with an 8-2 hexane-ethyl acetate mixture. The product was chromatographed a second time over silica gel and was eluted with a 9-1 hexane-ethyl acetate mixture to obtain 5.86 g of tert.-butyl (1R,trans, ΔE or ΔZ) 2,2-dimethyl-3-[2-phenylthio-2-ethoxycarbonyl-ethenyl]-cyclopropane-carboxylate.

NMR Spectrum (deuterochloroform):
Peaks at 0.98–1.1–1.23 ppm and 4.0–4.12–4.23–4.35 ppm (hydrogens of ethoxy); at 1.2–1.23 ppm (hydrogens of geminal methyls); at 1.47 ppm (hydrogens of methyls of tert.-butyl); at 1.77–1.85 ppm (1-hydrogen of cyclopropyl); at 2.57–2.65 ppm and 2.73–2.8 ppm (3-hydrogen of cyclopropyl); at 6.9–7.1 ppm (ethylenic hydrogen); at 7.2 ppm (aromatic hydrogens).

STEP B: (1R,trans, ΔZ or ΔE) 2,2-dimethyl-3-[2-phenylthio-2-ethoxycarbonyl-ethenyl]-cyclopropane-carboxylic acid A mixture of 5.27 g of the product of Step A, 0.5 g of p-toluene sulfonic acid and 50 ml of toluene was refluxed for 45 minutes, was cooled and poured into water with stirring. The decanted aqueous phase was extracted with ether and the combined organic phases were evaporated to dryness under reduced pressure. The residue was chromatographed over silica gel and eluted with a 6-4 hexane-ethyl acetate mixture to obtain 3.32 g of (1R,trans ΔZ or ΔE) 2,2-dimethyl-3-[2-phenylthio-2-ethoxycarbonyl-ethenyl]-cyclopropane-carboxylic acid.

NMR Spectrum (deuterochloroform):

Peaks at 0.98–1.1–1.2 ppm and 3.9–4.05–4.2–4.28 ppm attributed to the hydrogens of the ethyl Peak at 1.27 ppm attributed to the hydrogens of the twin methyls Peaks at 1.8–1.9 ppm attributed to the hydrogen in position 1 of the cyclopropyl Peaks at 2.6–2.7–2.8–2.9 ppm attributed to the hydrogen in position 3 of the cyclopropyl Peaks at 6.9–7.1 ppm attributed to the ethylene hydrogen Peak at 7.2 ppm attributed to the hydrogens of the aromatic nucleus Peak at 8.5 ppm attributed to the hydrogen of the carboxyl Step C 1R,trans 3-(ΔE or ΔZ 2-phenylthio-2-ethoxycarbonylethenyl)-2,2-dimethyl carboxylate of (S) -cyano-1-(3-phenoxyphenyl)methyl By operating as in example 2, starting with the acid prepared at stage A and with the appropriate alcohol, the product sought is obtained. (m.p. 84° C.).

NMR Spectrum (deuterochloroform):

Peaks at 1.0–1.11–1.23 ppm and 3.96–4.08–4.2–4.3 ppm (hydrogens of ethyl); at 1.18–1.25 ppm (hydrogens of geminal methyls); at 1.89–1.98 ppm (1-hydrogen of cyclopropyl); at 2.7–2.8 ppm and 2.83–2.9 ppm (3-hydrogen of cyclopropyl); at 6.4 ppm (hydrogen of carbon attached to —CN); at 6.9–7.7 ppm (aromatic hydrogens).

EXAMPLE 25

(S)α-cyano-3-phenoxy-benzyl (1R,cis,ΔZ) 2,2-dimethyl-3-[2-phenylthio-2-ethoxycarbonyl-ethenyl]-cyclopropane-carboxylate STEP A: (1R,cis,ΔZ) 2,2-dimethyl-3-[1-hydroxy 2-phenylthio-2-ethoxycarbonyl ethyl]-cyclopropane-carboxylic acid 5.6 g of potassium tert.-butyrate and 50 ml of tetrahydrofuran were added at −60° C. to a solution of 5.25 g of ethyl phenylthio-acetate, 3.5 g of 1R,5S 6,6-dimethyl-4(R)-hydroxy-3-oxa-bicyclo-[3,1,0]-hexane-2-one and 100 ml of tetrahydrofuran and then, aqueous N hydrochloric acid was added thereto at less than −20° C. The mixture was poured with stirring into water and was extracted with methylene chloride. The organic phase was washed with water and evaporated to dryness under reduced pressure. The residue was chromatographed over silica gel and eluted with a 6-4 hexane-ethyl acetate mixture to obtain 3.5 g of (1R,cis, ΔZ) 2,2-dimethyl- 3-[2-phenylthio-2-ethoxycarbonyl ethyl]-cyclopropane-carboxylic acid.

NMR Spectrum (deuterochloroform):

Peaks at 1.1–1.35 ppm (hydrogens of geminal methyls); at 1.1–1.35 ppm (hydrogens of methyl of ethyl); at 1.11–1.77 ppm (1- and 3-hydrogens of cyclopropyl); at 3.7–4.66 (3-hydrogens of ethyl); at 3.7–4.67 ppm (hydrogens of methylene of ethyl); at 5.94 ppm (hydrogen of —OH); at 5.94 ppm (hydrogen of —COOH).

STEP B:

6,6-dimethyl-4-(1-phenylthio-1-ethoxycarbonyl-methyl)-3-bicyclo [3,1,0] hexane-2-one A mixture of 3.38 g of the product of Step A, 50 mg of p-toluene sulfonic acid and 100 ml of benzene was refluxed and 30 ml of benzene were distilled while refluxing for 90 minutes and the mixture was evaporated to dryness under reduced pressure. The residue was chromatographed over silica gel and eluted with a 6-4 hexane-ethyl acetate mixture to obtain 2.6 g of 6,6-dimethyl-4-(1-phenylthio-1-ethoxycarbonyl-methyl)-3-bicyclo [3,1,0]-hexane-2-one.

NMR Spectrum (deuterochloroform):

Peaks at 1.11–1.23–1.35 ppm and 4.05–4.16–4.28–4.45 ppm (hydrogens of ethyl); at 1.12–1.2 ppm (hydrogens of geminal methyls); at 1.95–2.41 ppm (1- and 3-hydrogens of cyclopropyl); at 3.7–3.8 ppm

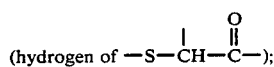

at 4.5–4.63 ppm

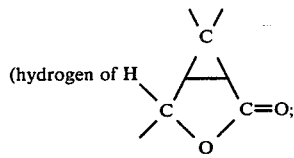

at 7.3–7.7 ppm (aromatic hydrogens).

STEP C: (1R,cis, ΔZ) 2,2-dimethyl-3-[2-phenylthio-2-ethoxycarbonyl-ethenyl]-cyclopropane-carboxylic acid A mixture of 2.2 g of the product of Step B, 2 ml of triethylamine and 22 ml of benzene was refluxed for 3 hours, cooled to 20° C. and admixed with aqueous N hydrochloric acid. The decanted organic phase was washed with water and evaporated to dryness under reduced pressure. The residue was chromatographed over silica gel and eluted with a 8-2 methylene chloride-ethyl acetate mixture to obtain 1.1 g of (1R,cis,ΔZ) 2,2-dimethyl-3-[2-phenylthio-2-ethoxycarbonyl-ethenyl]-cyclopropane-carboxylic acid melting towards 50° C.

NMR Spectrum (deuterochloroform):

Peaks at 1.02–1.13–1.25 ppm and 4–4.2–4.23–4.35 ppm (hydrogens of ethyl); at 1.22–1.38 ppm (hydrogens of geminal methyls); at 1.9–2.04 ppm (1-hydrogen of cyclopropyl); at 2.8–3.0 ppm (3-hydrogen of cyclopropyl); at 7.3 ppm (aromatic hydrogens); at 7.7–7.9 ppm (ethylenic hydrogen).

STEP D: (S)α-cyano-3-phenoxy-benzyl (1R,cis, ΔZ) 2,2-dimethyl-3-[2-phenylthio-2-ethoxycarbonyl-ethenyl]-cyclopropane-carboxylate Using the procedure of Example 2, the product of Step C and (S)α-cyano-3-phenoxy-benzyl alcohol were reacted to obtain (S)α-cyano-3-phenoxy-benzyl (1R,cis, ΔZ) 2,2-dimethyl-3-[2-phenylthio-2-ethoxycarbonyl-ethenyl]-cyclopropane-carboxylate.

NMR Spectrum (deuterochloroform):

Peaks at 1.18–1.27 ppm (hydrogens of geminal methyls); at 2.5–2.8 ppm (1-hydrogen of cyclopropyl); at 1.92-2.05 ppm (3-hydrogen of cyclopropyl); at 7.6-7.8 ppm (ethylenic hydrogen); at 6.48 ppm (hydrogen on carbon attached to —CN); at 1.03-1.15-1.27 ppm and 4.02-4.13-4.25-4.36 ppm (hydrogens of ethoxy); at 7.3 ppm (aromatic hydrogens of phenylthio); at 6.92 to 7.6 ppm (aromatic hydrogens of phenoxyphenyl).

EXAMPLE 26

(S)α-cyano-3-phenoxy-benzyl (1R,cis, ΔE) 2,2-dimethyl-3-[2-methylthio-2-ethoxycarbonyl-ethenyl]-cyclopropane-carboxylate Using the procedure of Example 2, the E isomer of Step C of Example 22 and (S)α-cyano-3-phenoxy-benzyl alcohol were reacted to obtain (S)α-cyano-3-phenoxy-benzyl (1R,cis,ΔE) 2,2-dimethyl-3-[2-methylthio-2-ethoxycarbonyl-ethenyl]-cyclopropane-carboxylate.

NMR Spectrum (deuterochloroform):
Peaks at 1.25-1.26 ppm (hydrogens of geminal methyls); at 1.25-1.37-1.48 ppm and 4.1-4.2-4.4-4.5 ppm (hydrogens of ethoxy); at 1.85-2.0 ppm (1-hydrogen of cyclopropyl); at 2.25 ppm (hydrogens of CH₃S—); at 2.8-3.2 ppm (3-hydrogen of cyclopropyl); at 6.1-6.3 ppm (ethylenic hydrogen); at 6.4 ppm (hydrogen of carbon attached to —CN); at 6.9-7.6 ppm (aromatic hydrogens).

EXAMPLE 27

Diastereoisomers A and B of (S)α-cyano-3-phenoxy-benzyl (1R,trans,ΔZ) 2,2-dimethyl-3-[2-methylsulfinyl-2-methoxycarbonyl-ethenyl]-cyclopropane-carboxylate

STEP A: (1R,trans ΔE and ΔZ) 2,2-dimethyl-3-[2-methylthio-2-methoxycarbonyl-ethenyl]-cyclopropane-carboxylic acid A solution of 14 g of potassium methylate in 100 ml of methanol was added at 10° C. to a mixture of 14.2 g of (1R,trans) 2,2-dimethyl-3-formyl-cyclopropane-carboxylic acid, 13.2 g of methyl methylthioacetate and 100 ml of methanol and the mixture was stirred at 20° C. for 18 hours and was evaporated to dryness under reduced pressure. The residue was chromatographed over silica gel and was eluted with a 1-1 cyclohexane-ethyl acetate mixture to obtain 5.2 g of (1R,trans ΔE and ΔZ) 2,2-dimethyl-3-[2-methylthio-2-methoxycarbonyl-ethenyl]-cyclopropane-carboxylic acid.

STEP B: (S)α-cyano-3-phenoxy-benzyl (1R,trans, ΔZ and ΔE) 2,2-dimethyl-3-[2-methylthio-2-methoxycarbonyl-ethenyl]-cyclopropane-carboxylate 4.26 g of dicyclohexylcarbodiimide and 1.95 ml of pyridine were added to a mixture of 5.1 g of the acid of Step A in 70 ml of methylene chloride and the mixture was stirred at 20° C. for 15 minutes after which 4.7 of (S)α-cyano-3-phenoxy-benzyl alcohol were added thereto. The mixture was stirred at 20° C. for 18 hours and was filtered. The filtrate was evaporated to dryness under reduced pressure and the residue was chromatographed over silica gel. Elution with benzene yielded 6.4 g of (S)α-cyano-3-phenoxy-benzyl (1R,trans,ΔZ and ΔE) 2,2-dimethyl-3-[2-methylthio-2-methoxycarbonyl-ethenyl]-cyclopropane-carboxylate.

STEP C: Diastereoisomers A and B of (S)α-cyano-3-phenoxybenzyl (1R,trans,ΔZ) 2,2-dimethyl-3-[2-methylsulfinyl-2-methoxycarbonyl-ethenyl]-cyclopropane-carboxylate A mixture of 6 g of the product of Step B, a solution of 5.7 g of sodium metaperiodate in 60 ml of water and 200 ml of methanol was stirred at 20° C. for 24 hours and after the addition of 1.8 g of sodium metaperiodate, the mixture was stirred at 20° C. for 18 hours and was filtered. The filtrate was evaporated to dryness under reduced pressure and the residue was chromatographed over silica gel. Elution with a 1-1 cyclohexane-ethyl acetate mixture yielded 0.5 g of the diastereoisomer A with a specific rotation of $[\alpha]_D^{20} = +152.5°$ (c=1.0% in benzene) and 0.5 g of the diastereoisomer B with a specific rotation of $[\alpha]_D^{20} = +57.5°$ (c=0.3% in benzene).

EXAMPLE 28

(S)αcyano-3-phenoxy-benzyl (1R,trans,ΔE) 2,2-dimethyl-3-[2-methoxy-2-isopropoxycarbonyl-ethenyl]-cyclopropane-carboxylate 15 ml of a methylene chloride solution containing 1.26 g of dicyclohexylcarbodiimide and 100 mg of 4-dimethylamino-pyridine were added at 0° C. to a solution of 1.5 g of (1R,trans,ΔE) 2,2-dimethyl-3-[2-methoxy-2-isopropoxycarbonyl-ethenyl]-cyclopropane-carboxylic acid [prepared as described in Example 16 for ΔZ isomer), 1.19 g of (S)α-cyano-3-phenoxybenzyl alcohol in 15 ml of methylene chloride and the mixture was stirred at room temperature for 16 hours and was vacuum filtered. The filter was rinsed with methylene chloride and the filtrate was evaporated to dryness under reduced pressure. The 2.95 g of residue were chromatographed over silica gel and eluted with an 8-2 hexane-methyl acetate mixture to obtain 1.58 g of (S)α-cyano-3-phenoxy-benzyl [1R,trans,ΔE) 2,2-dimethyl-3-[2-methoxy-2-isopropoxycarbonyl-ethenyl]-cyclopropane-carboxylate with a specific rotation of $[\alpha]_D^{20} = +2°$ (c=0.5 % in chloroform).

EXAMPLE 29

Using the procedure of Example 28, (1R,trans,ΔZ) 2,2-dimethyl-3-[2-methoxy-2-methoxycarbonyl-ethenyl]-cyclopropane-carboxylic acid and 1-(2-pyridyl-3-phenoxy)-methanol were reacted to obtain 1-(2-pyridyl-3-phenoxy)-methyl (1R,trans,ΔZ) 2,2-dimethyl-3-[2-methoxy-2-methoxycarbonyl-ethenyl] -cyclopropane-carboxylate with a specific rotation of $[\alpha]_D^{20} = +22°$ (c=1.2% in chloroform).

EXAMPLE 30

A and B diastereoisomers of (S)α-cyano-3-phenoxy-benzyl (1R, cis,ΔE) 2,2-dimethyl-3-[2-methylsulfinyl-2-methoxycarbonyl-ethenyl]-cyclopropane-carboxylate

STEP A:
6,6-dimethyl-4-(methoxycarbonylsulfinylmethyl)-3-oxa-bicyclo[3,1,0]hexane-2-one 5.44 g of methyl methylsulfinylacetate and 3.4 ml of pyrrolidine were added to a solution of 5.68 g of (1R,5S) 6,6-dimethyl-4(R)-hydroxy-3-oxa-bicyclo [3,1,0] hexane-2-one in 50 ml of methylene chloride and the mixture was stirred at 20° C. for 18 hours, was washed with aqueous N hydrochloric acid and evaporated to dryness under reduced pressure. The residue was chromatographed over silica gel and eluted with a 100-2 ethyl acetate-acetic acid mixture to obtain 6.1 g of 6,6-dimethyl-4-(methoxycarbonylsulfinylmethyl)-3-oxa-bicyclo[3,1,0] hexane-2-one.

STEP B: (S)α-cyano-3-phenoxy-benzyl (1R cis ΔE) 2,2-dimethyl-3-[2-methylsulfinyl-2-methoxycarbonyl-ethenyl]-cyclopropane-carboxylate 4.76 g of dicylohexylcarbodiimide were added to a mixture of 6.1 g of the product of Step A, 2.1 ml of pyridine and 70 ml of methylene chloride and after stirring for 15 minutes, 5.26 g of (S)α-cyano-3-phenoxy-benzyl alcohol were added to the mixture. The mixture was stirred at 20° C. for 18 hours and was filtered and the filtrate was evaporated to dryness under reduced pressure. The residue was chromatographed over silica gel and was eluted with a 6-4 cyclohexane-ethylacetate mixture to obtain 2.6 g of the diastereoisomer A of the (S)α-cyano-3-phenoxy-benzyl (1R,cis,ΔE) 2,2-dimethyl-3-[2-methylsulfinyl-2-methoxycarbonyl-ethenyl]-cyclopropane-carboxylate with a specific rotation of $[\alpha]_D^{20} = +156°$ (c=0.3% in benzene) and 2.2 g of the diastereoisomer B with a specific rotation of $[\alpha]_D^{20} = -9.5°$ (c=1% in benzene).

EXAMPLE 31

A and B diastereoisomers of (S)α-cyano-3-phenoxy-benzyl (1R, trans,ΔE) 2,2-dimethyl-3-[2-methylsulfinyl-2-methoxycarbonyl-ethenyl]-cyclopropane-carboxylate STEP A: (1R,trans,ΔE) 2,2-dimethyl-3-[2-methylsulfinyl-2-methoxycarbonyl-ethenyl]-cyclopropane-carboxylic acid 3.4 ml of pyrrolidine were added to a solution of 5.44 g of methyl methylsulfinyl-acetate, 5.68 g of 1R,trans 2,2-dimethyl-3-formyl-cyclopropane-carboxylic acid and 50 ml of methylene chloride and the mixture was stirred at 20° C. for 18 hours after which methylene chloride was added. The mixture was washed with aqueous N hydrochloric acid and was evaporated to dryness under reduced pressure. The residue was chromatographed over silica gel and was eluted with a 100-2 ethyl acetate-acetic acid mixture to obtain 6.2 g of (1R trans,ΔE) 2,2-dimethyl-3-[2methylsulfinyl-2-methoxycarbonyl-ethenyl]-cyclopropane-carboxylic acid with a specific rotation of $[\alpha]_D^{20} = +106.5°$ (c=1% in benzene).

STEP B: (S)α-cyano-3-phenoxy-benzyl (1R,trans,ΔE) 2,2-dimethyl-3-[2-methylsulfinyl-2-methoxycarbonyl-ethenyl]-cyclopropan-carboxylate A mixture of 5.6 g of the product of Step A, 1.95 ml of pyridine, 4.4 g of dicyclohexylcarbodiimide and 60 ml of methylene chloride was stirred at 20° C. for 15 minutes and 4.84 g of (S)α-cyano-3-phenoxy-benzyl alcohol were added thereto. The mixture was stirred at 20° C. for 16 hours and was filtered and the filtrate was evaporated to dryness under reduced pressure. The residue was chromatographed over silica gel and was eluted with a 6-4 cyclohexane-ethyl acetate mixture to obtain 1.0 g of the diastereoisomer A of (S)α-cyano-3-phenoxy-benzyl (1R,trans ΔE) 2,2-dimethyl-3-[2-methylsulfinyl-2-methoxycarbonyl-ethenyl]-cyclopropane-carboxylate with a specific rotation of $[\alpha]_D^{20} = +26.5°$ (c=0.5% in benzene) and 1.1 g of the diastereoisomer B with a specific rotation of $[\alpha]_D^{20} = +130°$ (c=0.5% in benzene).

EXAMPLE 32

(S)α-cyano-3-phenoxy-benzyl (1R,trans,ΔE) 2,2-dimethyl-3-[2-methylsulfonyl-2-methoxycarbonyl-ethenyl]-cyclopropane-carboxylate 431 mg of m-chloro-perbenzoic acid were added at −20° C. to a solution of 1.2 of (S)α-cyano-3-phenoxy-benzyl (1R,trans,ΔE) 2,2-dimethyl-3-[2-methylsulfinyl-2-methoxy carbonyl-ethenyl]-cyclopropane-carboxylate in 30 ml of methylene chloride and the mixture was stirred for 2 hours at 20° C. and was filtered. The filtrate was evaporated to dryness under reduced pressure and the residue was chromatographed over silica gel. Elution with a 6-4 cyclohexane-ethyl acetate mixture yielded 0.8 g of (S)α-cyano-3-phenoxy-benzyl (1R,trans,ΔE) 2,2-dimethyl-3-[2-methylsulfonyl-2-methoxycarbonyl-ethenyl]-cyclopropane-carboxylate with a specific rotation of $[\alpha]_D^{20} = +73°$ (c=0.3% in benzene).

EXAMPLE 33

Using the procedure of Example 32, (S)α-cyano-3-phenoxy-benzyl (1R,cis,ΔE) 2,2-dimethyl-3-[2-methylsulfinyl-2-methoxycarbonyl-ethenyl]-cyclopropane-carboxylate was reacted to obtain (S)α-cyano-3-phenoxy-benzyl (1R,cis,ΔE) 2,2-dimethyl-3-[2-methylsulfonyl-2-methoxycarbonyl-ethenyl]-cyclopropane-carboxylate melting at 70° C. and having a specific rotation of $[\alpha]_D^{20} = +77°$ (c=0.4% in benzene).

EXAMPLE 34

STEP A: (1R,cis,ΔZ) 2,2-dimethyl-3-[2-methylthio-2-methoxycarbonyl-ethenyl]-cyclopropane-carboxylic acid A solution of 8.97 g of potassium tert.-butylate in 50 ml of tetrahydrofuran was slowly added at −60° C. to a solution of 5.6 of (1R,5S) 6,6-dimethyl-4(R)-hydroxy-3-oxa-bicyclo[3,0,1]hexane-2-one, 5.28 g of methyl methylthioacetate and 75 ml of tetrahydrofuran and the mixture was stirred at −60° C. for one hour and was admixed with saturated aqueous monosodium phosphate. The mixture was extracted with ethyl acetate and the organic phase was evaported to dryness under reduced pressure. The residue was taken up in benzene and 100 mg of p-toluene sulfonic acid were added thereto. The mixture was refluxed for 90 minutes and water was removed by azeotropic distillation. 12 ml of triethylamine were added to the mixture which was then refluxed for 3 hours and evaporated to dryness under reduced pressure. The residue was chromatographed over silica gel and was eluted with a 1-1 cyclohexane-ethyl acetate mixture to obtain 6.3 g of (1R,cis,ΔZ) 2,2-dimethyl-3-[2-methylthio-2-methoxycarbonyl-ethenyl]-cyclopropane-carboxylic acid containing 10% of ΔE isomer according to its NMR spectrum.

NMR Spectrum (deuterochloroform):

Peaks at 1.32–1.35 ppm (hydrogens of geminal methyls); at 1.9–2.1 ppm (1-hydrogen of cyclopropyl); at 2.23 ppm (hydrogens of $CH_3S$—); at 2.52–2.83 ppm (3-hydrogen of cyclopropyl); at 3.85 ppm (hydrogens of $CH_3O$—); at 6.3–6.5 ppm (ethylenic hydrogen −0.1 of ΔE); at 7.4–7.6 ppm (ethylenic hydrogen—0.9 of ΔZ).

STEP B: (S)α-cyano-3-phenoxy-benzyl (1R,cis,ΔZ) 2,2-dimethyl-3-[2-methylthio-2-methoxycarbonyl-ethenyl]-cyclopropanecarboxylate A mixture of 5.26 g of dicyclohexylcarbodiimide, 6.3 g of the product of Step A and 75 ml of methylene chloride was stirred at 20° C. for 15 minutes and 5.8 g of (S)α-cyano-3-phenoxy-benzyl alcohol and 2.4 ml of pyridine were added thereto. The mixture was stirred at 20° C. for 18 hours and was filtered and the filtrate was evaporated to dryness under reduced pressure. The residue was chromatographed over silica gel and was eluted with a 9-1 cyclohexane-ethyl acetate mixture to obtain 6.8 g of (S)α-cyano-3-phenoxy-benzyl (1R,cis,ΔZ)2,2-dimethyl-3-[2-methylthio-2-methoxycarbonyl-ethenyl]-cyclopropane-carboxylate and 0.8 g of the ΔE isomer.

| Circular dichroism (dioxane): | |
|---|---|
| ΔZ isomer | |
| max. at 257 nm | Δε = +1.15 |
| max. at 290 nm | Δε = +1.0 |
| max. at 305 nm | Δε = +0.9 |
| ΔE isomer | |
| max. at 240 nm | Δε = −0.6 |
| max. at 275 nm | Δε = −0.25 |
| max. at 300 nm | Δε = −0.6 |

STEP C: A and B diastereoisomers of (S)α-cyano-3-phenoxybenzyl (1R,cis,ΔZ) 2,2-dimethyl-3-[2-methylsulfinyl-2-methoxycarbonyl-ethenyl]-cyclopropane-carboxylate Using the procedure of Example 27, (S)α-cyano-3-phenoxy-benzyl (1R,cis,ΔZ) 2,2-dimethyl-3-[2-methylthio-2-methoxycarbonyl-ethenyl]-cyclopropane-carboxylate was reacted to obtain the diastereoisomer A of (S)α-cyano-3-phenoxy-benzyl (1R,cisΔZ) 2,2-dimethyl-3-[2-methylsulfinyl-2-methoxycarbonylethenyl]-cyclopropane-carboxylate with a specific rotation of $[\alpha]_D^{20} = +73°$ (c=1% in benzene) and the diastereoisomer B with a specific rotation of $[\alpha]_D^{20} = +52°$ (c=1% in benzene).

EXAMPLE 35

(S)α-cyano-3-phenoxy-benzyl (1R,cis,ΔZ) 2,2-dimethyl-3-[2-methylsulfonyl-2-methoxycarbonyl-ethenyl]-cyclopropane-carboxylate Using the procedure of Example 32, (S)α-cyano-3-phenoxy-benzyl (1R,cis,ΔZ) 2,2-dimethyl-3-[2-methylsulfinyl-2-methoxycarbonyl-ethenyl]-cyclopropane-carboxylate was reacted to obtain (S)α-cyano-3-phenoxy-benzyl (1R,cis,ΔZ) 2,2-dimethyl -3-[2-methylsulfonyl-2-methoxycarbonyl-ethenyl]-cyclopropane-carboxylate with a specific rotation of $[\alpha]_D^{20} = +15°$ (c=1% in benzene).

EXAMPLE 36

Using the procedure of Example 28, (1R,trans,ΔE) 2,2-dimethyl-3-[2-methoxy-2-methoxycarbonyl-ethenyl]-cyclopropane carboxylic acid and (6-phenoxy-2-pyridyl)-methanol were reacted to obtain (6-phenoxy-2-pyridyl)-methyl(1R,trans,ΔE), 2,2-dimethyl-3-[2-methoxy-2-methoxycarbonyl-ethenyl]-cyclopropane-carboxylate with a specific rotation of $[\alpha]_D^{20} = +9°$ (c=0.7% in chloroform).

EXAMPLE 37

(S)α-cyano-3-phenoxy-benzyl (1R,trans,ΔZ) 2,2-dimethyl-3-[2-methoxy-2-tert.-butoxycarbonyl-ethenyl]-cyclopropane-carboxylate STEP A: E and Z isomers of methoxy-methyl (1R,trans,ΔZ) 2,2-dimethyl-3-[2-methoxy-2-tert.-butoxycarbonyl-ethenyl]-cyclopropane-carboxylate A solution of 2.13 g of methyl 0,0-diethyl-phosphono-tert.-butoxyacetate in 3 ml of tetrahydrofuran was added at 0° C. to a mixture of 0.88 g of potassium tert.-butylate, 4 ml of tert.-butanol, 2 ml of dimethylformamide and 4 ml of tetrahydrofuran and the mixture was stirred at 0° C. for 30 minutes after which a solution of methoxymethyl(1R,trans,ΔZ) 2,2-dimethyl-3-formyl-cyclopropane-carboxylate in 6 ml of tetrahydrofuran was added thereto at 0° C. The mixture was stirred at 0° C. for one hour and was poured into water. The mixture was extracted with isopropyl ether with stirring. The decanted organic phase was evaporated to dryness under reduced pressure and the residue was chromatographed over silica gel. Elution with a 95-5 benzene-ethyl acetate mixture yielded 0.97 g of methoxymethyl (1R,trans,ΔZ) 2,2-dimethyl-3-[2-methoxy-2-tert.butoxycarbonyl-ethenyl]-cyclopropane-carboxylate and 0.45 g of the E isomer.

NMR Spectrum (deuterochloroform):

Z isomer:

Peaks at 1.25–1.32 ppm (hydrogens of geminal methyls); at 1.32 ppm (hydrogens of methyls of tert-.butyl); at 1.66–1.76 ppm (1-hydrogen of cyclopropyl); at 2.4 to 2.65 ppm (3-hydrogen of cyclopropyl); at 3.75 ppm

at 3.5 ppm (hydrogens of CH₃OCH₂—); at 5.25 ppm (hydrogens of —CH₂— of CH₃O—CH₂—); at 6.0–6.2 ppm (ethylenic hydrogen).

E isomer:

Peaks at 1.18–1.32 ppm (hydrogens of geminal methyls); at 1.25 ppm (hydrogens of methyls of tert.-butyl); at 1.5–1.6 ppm (1-hydrogen of cyclopropyl); at 2.68 to 2.93 ppm (3-hydrogen of cyclopropyl); at 3.5 ppm (hydrogens of CH₃O—CH₂); at 3.8 ppm

at 5.25 ppm (hydrogens of methylene of CH₃O—CH₂—); at 5.4–5.5 ppm (ethylenic hydrogen).

STEP B: (1R,trans,ΔZ) 2,2-dimethyl-3-[2-methoxy-2-tert.-butoxycarbonyl-ethenyl]-cyclopropane-carboxylic acid A mixture of 910 mg of Z isomer of Step A, 17.5 ml of methanol, 17.5 ml of acetone and 35 ml of aqueous N sodium hydroxide solution was stirred for 6½ hours at 20° C. and was then poured into water. The mixture was extracted with ether and the organic phase was evaporated to dryness under reduced pressure. The residue was chromatographed over silica gel and was eluted with a 4-6 hexane-ethyl acetate mixture to obtain 0.47 g of (1R,trans,ΔZ) 2,2-dimethyl-3-[2-methoxy-2-tert.- butoxycarbonyl-ethenyl]-cyclopropane-carboxylic acid.

IR Spectrum (ethanol):
Absorption at 3500 cm$^{-1}$ (mono and dimer acid); at 1725 cm$^{-1}$ (ester carbonyl); at 1695 cm$^{-1}$ (acid carbonyl); at 1640 cm$^{-1}$ ($\Delta Z$ C=C); at 1440 cm$^{-1}$ (COOCH$_3$bond); at 1372 cm$^{-1}$ (tert.-butyl).

STEP C: (S)α-cyano-3-phenoxy-benzyl (1R, trans,ΔZ) 2,2-dimethyl-3-[2-methoxy-2-tert.-butoxycarbonyl-ethenyl]-cyclocarboxylate Using the procedure of Example 28, the product of Step B and (S)α-cyano-3-phenoxy-benzyl alcohol were reacted to obtain (S)α-cyano-3-phenoxy-benzyl (1R,trans,ΔZ) 2,2-dimethyl-3-[2-methoxy-2-tert.-butoxycarbonyl-ethenyl]-cyclocarboxylate melting at 72° C. and having a specific rotation of $[\alpha]_D^{20} = -90°$ (c=0.7% in chloroform).

EXAMPLE 38

(S)α-cyano-3-phenoxy-benzyl (1R,trans,ΔZ) 2,2-dimethyl-3-[2-tert.-butoxy-2-tert.-butoxycarbonyl-ethenyl]-cyclopropane-carboxylate

STEP A: Methoxymethyl (1R,trans) 2,2-dimethyl-3-formyl-cyclopropane-carboxylate A mixture of 1.64 g of lithium hydride and 25.6 g of (1R,trans) 2,2-dimethyl-3-formyl-cyclopropane-carboxylic acid and 25 ml of tetrahydrofuran was stirred at 15° C. for 30 minutes and then 18.2 g of a freshly prepared chloromethyl methyl ether (0.225 mols) were added thereto. The mixture was stirred at 20° C. for 4 hours and was then poured into a mixture of ice, water and sodium bicarbonate with stirring. The mixture was extracted with isopropyl ether and the organic phase was evaporated to dryness under reduced pressure. The residue was rectified under vacuum to obtain 15.15 g of methoxymethyl (1R,trans) 2,2-dimethyl-3-formyl-cyclopropane-carboxylate with a boiling point of 67° C. at 0.05 mm Hg.

STEP B: Methoxymethyl (1R,trans,ΔZ) 2,2-dimethyl-3-[2-tert.-butoxy-2-tert.-butoxycarbonyl-ethenyl]-cyclopropane-carboxylate A solution of 8.1 g of tert.-butyl 0,0-diethylphosphonotert.-butoxyacetate in 13.3 ml of tetrahydrofuran was added at 0° C. to a mixture of 2.8 g of potassium tert.-butyllate, 13.3 ml of tert.-butanol, 6.6 ml of dimethylformamide and 13.3 ml of tetrahydrofuran and the mixture was stirred at 0° C. for 30 minutes. A solution of 4.66 g of the product of Step B in 20 ml of tetrahydrofuran was added to the mixture which was stirred at −5° C. for one hour and was poured into water. The mixture was extracted with isopropyl ether and the organic phase was evaporated to dryness under reduced pressure. The residue was chromatographed over silica gel and was eluted with an 8-2 hexane-ethyl acetate mixture to obtain 0.59 g of methoxymethyl (1R,trans,ΔZ) 2,2-dimethyl-3-[2-tert.butoxy-2-tert.butoxycarbonyl-ethenyl]-cyclopropane-carboxylate.

STEP C: (1R,transΔZ) 2,2-dimethyl-3-[2-tert.-butoxy-2-tert.butoxycarbonyl-ethenyl]-cyclopropane-carboxylic acid A mixture of 590 mg Sof the product of Step B, 20 ml of methanol, 10 ml of acetane and 20 ml of aqueous N hydrochloric acid was stirred at 20° C. for 6 hours and was poured into water. The mixture was extracted with methylene chloride and the organic phase was evaporated to dryness under reduced pressure. The residue was chromatographed over silica gel and was eluted with a 4-6 hexane-ethyl acetate mixture to obtain 364 mg of (1R,transΔZ) 2,2-dimethyl-3-[2-tert.-butoxy-2-tert.-butoxycarbonyl-ethenyl]-cyclopropane-carboxylic acid melting at 85° C.

STEP D: (S)α-cyano-3-phenoxy-benzyl (1R,trans,ΔZ) 2,2-dimethyl-3-[2-tert.butoxy-2-tert.-butoxycarbonyl-ethenyl]-cyclopropane-carboxylate Using the procedure of Example 28, the product of Step C and (S)α-cyano-3-phenoxy-benzyl alcohol were reacted to obtain (S)α-cyano-3-phenoxy-benzyl (1R,trans,ΔZ) 2,2-dimethyl-3-[2-tert.-butoxy-2-tert.-butoxycarbonyl-ethenyl]cyclopropane-carboxylate melting at 81° C. and having a specific rotation of $[\alpha]_D^{20} = -9°$ (c=0.5% in chloroform).

EXAMPLE 39

(S)α-cyano-3-phenoxy-benzyl (1R,trans,ΔE) 2,2-dimethyl-3-[2-tert. -butoxy-2-methoxy carbonyl-ethenyl]-cyclopropane-carboxylate A mixture of 410 mg of methoxymethyl (1R,trans,ΔE) 2,2-dimethyl-3-[2-tert.-butoxy-2-methoxy carbonyl-ethenyl]cyclopropane-carboxylate, 8 ml of methanol, 8 ml of acetone and 16 ml of aqueous N hydrochloric acid was stirred at 20° C. for 6 hours and was poured into water. The mixture was extracted with ether and the organic phase was evaporated to dryness under reduced pressure to obtain 300 mg of (1R,trans,ΔE) 2,2-dimethyl-3-[2-tert.-butoxy-2-methoxy carbonyl-ethenyl]cyclopropane-carboxylic acid.

Using the procedure of Example 28, the said acid and (S)α-cyano-3-phenoxy-benzyl alcohol were reacted to obtain (S)α-cyano-3-phenoxy-benzyl (1R,trans,ΔE) 2,2-dimethyl-3-[2-tert.-butoxy-2-methoxy carbonyl-ethenyl]-cyclopropane-carboxylate melting at 80° C. and having a specific rotation of $[\alpha]_D^{20} = +7°$ (c=1% in chloroform).

EXAMPLE 40

A soluble concentrate was prepared by homogenizing a mixture of 0.25 g of the product of Example 7, 1 g of piperonyl butoxide, 0.25 g of Tween 80, 0.1 g of Topanol A and 98.4 g of water.

An emulsifiable concentration was prepared by intimately mixing 0.015 g of the compound of Example 39, 0.5 g of piperonyl butoxide, 0.1 g of Topanol A and 99.385 g of xylene.

An emulsifiable concentrate was also prepared by homogenizing a mixture of 1.5 g of the product of Example 9, 20 g of Tween 80, 0.1 g of Topanol A and 78.4 g of xylene.

A fumigant composition was prepared containing 0.25 g of the product of Example 3, 25 g of Tabu powder, 40 g of powdered cedar needles, 33.75 g of powdered pine wood, 0.5 g of brillant green and 0.5 g of p-nitrophenol.

KNOCKDOWN ACTIVITY AGAINST HOUSEFLIES

The test insects were 4 day old female houseflies which were directly sprayed in a Kearns and March chamber with 0.25 g/l of the active compound in a mixture of Isopar L (petroleum solvent) containing 5% acetone using 2 ml in one second. 50 insects were used for each test and readings were taken every minute for 10 minutes and then at 15 minutes to determine the KT₅₀ by known methods. The results are reported in the following Table.

TABLE

| Compound of Example | KT₅₀ in minutes |
|---|---|
| 3 | 1.2 |
| 6 | 3.5 |
| 7 | 3 |
| 8 | 2.8 |
| 9 | 2.2 |
| 10 | 5.0 |
| 11 | 1.1 |
| 15 | 2.1 |
| 18 | 3 |
| 19 | 2.5 |
| 28 | 8.45 |
| 29 | 8.33 |
| 30 stereoisomer B | 8.1 |
| 32 | 7.5 |
| 34 stereoisomer A | 6.2 |
| 39 | 3.0 |

Various modifications of the products and methods of the invention may be made without departing from the spirit or scope thereof and it is to be understood that the invention is to be limited only as defined in the appended claims.

What we claim is:

1. A compound selected from the group consisting of all stereoisomer forms and mixtures of stereoisomers of compounds of the formula

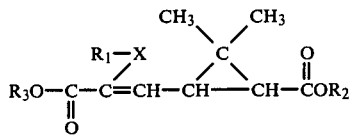

wherein X is selected from the group consisting of oxygen, sulfur, sulfoxide and sulfone, $R_1$ and $R_3$ are individually selected from the group consisting of alkyl of 1 to 7 carbon atoms, alkenyl and alkadienyl of 2 to 7 carbon atoms and cycloalkyl and cycloalkenyl of 3 to 7 carbon atoms optionally substituted with at least one halogen and optionally interrupted with at least one heteroatom and aryl and aralkyl of 6 to 18 carbon atoms and $R_2$ is selected from the group consisting of

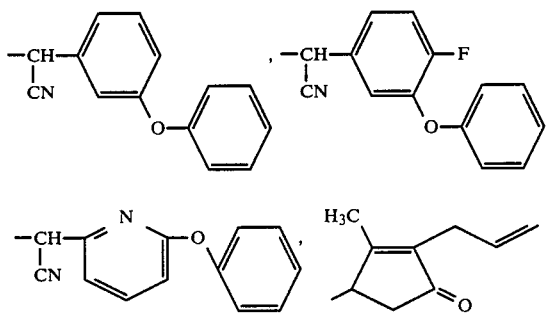

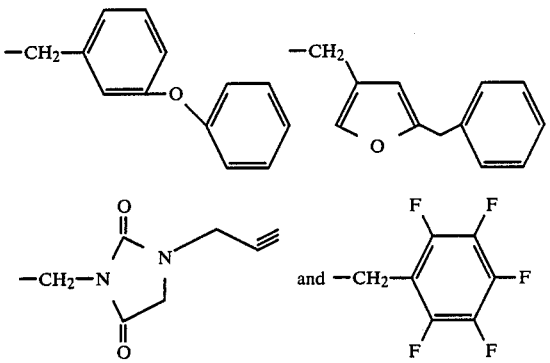

2. A compound of claim 1 wherein X is oxygen.
3. A compound of claim 1 wherein X is sulfur.
4. A compound of claim 1 selected from the group consisting of (S)α-cyano-3-phenoxy-benzyl (1R,trans,ΔZ) 2,2-dimethyl-3-dimethyl-3-[2-methoxy-2-methoxycarbonyl-ethenyl]-cyclopropane-carboxylate, (S)α-cyano-3-phenoxy-benzyl (1R,trans,ΔZ) 2,2-dimethyl-3-[2-methoxy-2-methoxycarbonyl-ethenyl]-cyclopropane-carboxylate, 3-allyl-2-methyl-4-oxo-2-cyclopenten-1-yl (1R,trans,ΔZ) 2,2-dimethyl-3-[2-methoxy-2-methoxycarbonyl-ethenyl]-cyclopropane-carboxylate, 3-alkyl-2-methyl-4-oxo-2-cyclopenten-1-yl (1R, trans,ΔE) 2,2-dimethyl-3-[2-methoxy-2-methoxycarbonyl-ethenyl]-cyclopropane-carboxylate, [1-(3-propyn-2-yl)-2,5-dioxo-imidazolidinyl]-methyl (1R,trans,ΔZ) 2,2-dimethyl-3-[2-methoxy-2-methoxycarbonyl-ethenyl]-cyclopropane-carboxylate, (S)α-cyano-3-phenoxy-4-fluoro-benzyl (1R, trans,ΔZ or ΔE) 2,2-dimethyl-3-[2-methoxy-2methoxycarbonyl-ethenyl]-cyclopropane-carboxylate, (R,S)α-cyano-6'-phenoxy- 2'-pyridyl-methyl (1R,trans,ΔZ or ΔE) 2,2-dimethyl -3-[2-methoxy-2-methoxycarbonyl-ethenyl]-cyclopropane-carboxylate, (S)α-cyano-3-phenoxy-benzyl (1R,trans,ΔZ) 2,2-dimethyl-3-[2-methoxy-2-ethoxycarbonyl-ethenyl]-cyclopropane-carboxylate, (S)α-cyano-3-phenoxy-benzyl (1R,trans,ΔZ) 2,2-dimethyl-3-[2-methoxy-2-methoxycarbonyl-ethenyl]-cyclopropane-carboxylate, (S)α-cyano 3-phenoxy-benzyl (1R, cisΔZ) 2,2-dimethyl 3-[2-methoxy 2-methoxycarbonyl ethenyl cyclopropane carboxylate, A and B stereoisomers of (S)α-cyano -3-phenoxy-benzyl (1R, cis,ΔZ) 2,2-dimethyl-3-2-methylsulfinyl-2-methoxycarbonyl-ethyenyl]-cyclopropane-carboxylate and (S)α-cyano-3-phenoxy-benzyl (1R,trans,ΔE) 2,2-dimethyl-3-[2-tert.-butoxy-2-methoxycarbonyl-ethenyl]-cyclopropane-carboxylate.

5. A compound of the formula

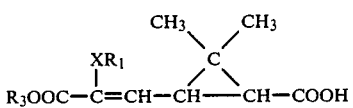

wherein X is selected from the group consisting of —O—, —S—, sulfoxide and sulfone and $R_1$ and $R_3$ are selected from the group consisting of alkyl of 1 to 7 carbon atoms, alkenyl and alkadienyl of 2 to 7 carbon atoms cycloalkyl and cycloalkenyl of 3 to 7 carbon atoms optionally substituted with at least one halogen and optionally interrupted with at least one heteroatom and aryl and aralkyl of 6 to 18 carbon atoms.

6. A compound of claim 5 selected from the group consisting of (1R,trans,ΔE) 2,2-dimethyl-3-[2-methoxy-2-methoxycarbonyl-ethenyl]-cyclopropane-carboxylic acid, (1R,trans,ΔZ) 2,2-dimethyl-3-[2-methoxy-2-methoxycarbonyl-ethenyl]-cyclopropane-carboxylic acid, (1R,trans,ΔZ) 2,2-dimethyl-3-[2-methylthio-2-ethoxycarbonyl-ethenyl]-cyclopropane-carboxylic acid, (1R,trans,ΔE or ΔZ) 2,2-dimethyl -3-[2-phenylthio-2-ethoxycarbonyl-ethenyl]-cyclopropane-carboxylic acid, (1R,trans,ΔE) 2,2-dimethyl-3-[2-ethoxy-2-ethoxycarbonyl-ethenyl]-cyclopropane-carboxylic acid, (1R,trans, ΔZ) 2,2-dimethyl-3-[2-ethoxy-2-ethoxycarbonyl-ethenyl]-cyclopropane-carboxylic acid, (1R,cis,ΔZ) 2,2-dimethyl-3-[2-phenylthio-2-ethoxycarbonyl-ethenyl]-cyclopropane-carboxylic acid, (1R,cis,ΔE or ΔZ) 2,2-dimethyl-3-[2-methoxy-2-methoxycarbonyl-ethenyl]-cyclopropane-carboxylic acid, (1R,cis,ΔE or ΔZ) 2,2-dimethyl-3-[2-methylthio-2-methoxycarbonyl-ethenyl]cyclopropane-carboxylic acid and (1R, trans,ΔE or ΔZ) 2,2-dimethyl-3-[2-methoxy-2-tert.-butoxycarbonyl-ethenyl]-cyclopropane-carboxylic acid.

7. An insecticidal composition comprising an insecticidally effective amount of at least one compound of claim 1 and an inert carrier.

8. A composition of claim 7 wherein X is oxygen.

9. A composition of claim 7 wherein X is sulfur.

10. A composition of claim 7 wherein the active compound is selected from the group consisting of (S)α-cyano-3-phenoxy-benzyl (1R,trans, Z) 2,2-dimethyl-3-[2-methoxy-2-methoxycarbonyl-ethenyl]-cyclopropanecarboxylate, (S)α-cyano-3-phenoxy-benzyl (1R,trans,ΔZ)2,2-dimethyl-3-[2-ethoxy-2-ethoxycarbonyl-ethenyl]-cyclopropane-carboxylate, 3-allyl-2-methyl-4-oxo-2-cyclopenten-1-yl (1R, trans,ΔZ) 2,2-dimethyl-3-[2-methoxy-2-methoxycarbonyl-ethenyl]-cyclopropane-carboxylate, 3-allyl-2-methyl-4-oxo-2-cyclopenten-1-yl (1R,trans,ΔE) 2,2-dimethyl-3-[2-methoxy-2-methoxycarbonyl-ethenyl]-cyclopropane-carboxylate, [1-(3-propyn-2-yl)-2,5-dioxo-imidazolidinyl]-methyl (1R,trans,ΔZ) 2,2-dimethyl-3-[2-methoxy-2-methoxycarbonyl-ethenyl]-cyclopropane-carboxylate, (S)α-cyano-3-phenoxy-4-fluoro-benzyl (1R,trans,ΔZ or ΔE) 2,2-dimethyl-3-[2-methoxy-2-methoxycarbonyl-ethenyl]-cyclopropane-carboxylate, (R,S)α-cyano-6'-phenoxy-2'-pyridyl-methyl (1R,trans,ΔZ or ΔE) 2,2-dimethyl -3-[2-methoxy-2-methoxycarbonyl-ethenyl]-cyclopropane-carboxylate, (S)α-cyano-3-phenoxy-benzyl (1R,trans,ΔZ) 2,2-dimethyl-3-[2-methoxy-2-ethoxycarbonyl-ethenyl]-cyclopropane-carboxylate, (S)α-cyano-3-phenoxy-benzyl (1R,trans,ΔZ) 2,2-dimethyl-3-[2-methoxy-2-methoxycarbonyl-ethenyl]-cyclopropane-carboxylate, (S)α-cyano 3-phenoxy-benzyl (1R,cisΔZ) 2,2-dimethyl 3-[2-methoxy 2-methoxycarbonyl ethenyl cyclopropane carboxylate, A and B steroisomers of (S)α-cyano -3-phenoxy-benzyl (1R,cis, ΔZ) 2,2-dimethyl-3-[2-methylsulfinyl-2-methoxycarbonyl-ethenyl]-cyclopropane-carboxylate and (S)α-cyano-3-phenoxy-benzyl (1R,trans,ΔE) 2,2-dimethyl-3-]2-tert.-butoxyl-2-methoxycarbonyl-ethenyl]-cyclopropane-carboxylate.

* * * * *